(12) United States Patent
Chatelier et al.

(10) Patent No.: US 9,739,749 B2
(45) Date of Patent: Aug. 22, 2017

(54) SYSTEM AND METHOD FOR MEASURING AN ANALYTE IN A SAMPLE

(71) Applicant: LifeScan, Inc., Milpitas, CA (US)

(72) Inventors: Ronald C. Chatelier, Bayswater (AU); Alastair M. Hodges, Blackburn South (AU); Santhanagopalan Nandagopalan, San Jose, CA (US)

(73) Assignee: LifeScan, Inc., Wayne, PA (US)

( * ) Notice: Subject to any disclaimer, the term of this patent is extended or adjusted under 35 U.S.C. 154(b) by 209 days.

(21) Appl. No.: 14/577,384

(22) Filed: Dec. 19, 2014

(65) Prior Publication Data

US 2015/0101928 A1     Apr. 16, 2015

Related U.S. Application Data

(60) Continuation of application No. 13/619,463, filed on Sep. 14, 2012, now Pat. No. 8,916,040, which is a
(Continued)

(51) Int. Cl.
*G01N 27/327* (2006.01)
*G01N 27/416* (2006.01)
*C12Q 1/00* (2006.01)

(52) U.S. Cl.
CPC ......... *G01N 27/4163* (2013.01); *C12Q 1/006* (2013.01); *G01N 27/3274* (2013.01)

(58) Field of Classification Search
CPC . G01N 27/4163; G01N 27/3274; C12Q 1/006
See application file for complete search history.

(56) References Cited

U.S. PATENT DOCUMENTS

| 3,648,160 A | 3/1972 | Beaver |
| 4,088,448 A | 5/1978 | Lilja et al. |

(Continued)

FOREIGN PATENT DOCUMENTS

| AU | 3104293 A | 7/1993 |
| AU | 5487394 | 8/1994 |

(Continued)

OTHER PUBLICATIONS

Japanese Office Action for JP 2014-098994; Dated: Jan. 13, 2015; 2 pages.

(Continued)

*Primary Examiner* — J. Christopher Ball
(74) *Attorney, Agent, or Firm* — Barclay Damon, LLP

(57) ABSTRACT

Methods of determining a corrected analyte concentration in view of some error source are provided herein. The methods can be utilized for the determination of various analytes and/or various sources of error. In one example, the method can be configured to determine a corrected glucose concentration in view of an extreme level of hematocrit found within the sample. In other embodiments, methods are provided for identifying various system errors and/or defects. For example, such errors can include partial-fill or double-fill situations, high track resistance, and/or sample leakage. Systems are also provided for determining a corrected analyte concentration and/or detecting some system error.

14 Claims, 14 Drawing Sheets

Related U.S. Application Data division of application No. 12/349,017, filed on Jan. 6, 2009, now Pat. No. 8,603,768.

(60) Provisional application No. 61/021,713, filed on Jan. 17, 2008.

(56) References Cited

U.S. PATENT DOCUMENTS

| | | |
|---|---|---|
| 4,224,125 A | 9/1980 | Nakamura et al. |
| 4,233,029 A | 11/1980 | Columbus |
| 4,250,257 A | 2/1981 | Lee et al. |
| 4,254,083 A | 3/1981 | Columbus |
| 4,259,165 A | 3/1981 | Miyake et al. |
| 4,301,412 A | 11/1981 | Hill et al. |
| 4,301,414 A | 11/1981 | Hill et al. |
| 4,303,887 A | 12/1981 | Hill et al. |
| 4,307,188 A | 12/1981 | White |
| 4,374,013 A | 2/1983 | Enfors et al. |
| 4,404,066 A | 9/1983 | Johnson |
| 4,431,004 A | 2/1984 | Bessman et al. |
| 4,436,812 A | 3/1984 | Endoh et al. |
| 4,508,613 A | 4/1985 | Busta et al. |
| 4,517,287 A | 5/1985 | Scheibe et al. |
| 4,517,291 A | 5/1985 | Seago |
| 4,533,440 A | 8/1985 | Kim |
| 4,545,382 A | 10/1985 | Higgins et al. |
| 4,547,735 A | 10/1985 | Kiesewetter |
| 4,552,840 A | 11/1985 | Riffer |
| 4,629,563 A | 12/1986 | Wrasidlo |
| 4,654,197 A | 3/1987 | Lilja et al. |
| 4,664,119 A | 5/1987 | Bessman et al. |
| 4,686,479 A | 8/1987 | Young |
| 4,711,245 A | 12/1987 | Higgins et al. |
| 4,774,039 A | 9/1988 | Wrasidlo |
| 4,790,925 A | 12/1988 | Miller et al. |
| 4,900,424 A | 2/1990 | Birth et al. |
| 4,919,770 A | 4/1990 | Preidel et al. |
| 4,963,815 A | 10/1990 | Hafeman |
| 5,059,908 A | 10/1991 | Mina |
| 5,064,516 A | 11/1991 | Rupich |
| 5,089,320 A | 2/1992 | Straus et al. |
| 5,108,564 A | 4/1992 | Szuminsky et al. |
| 5,120,420 A | 6/1992 | Nankai et al. |
| 5,122,244 A | 6/1992 | Hoenes et al. |
| 5,126,034 A | 6/1992 | Carter et al. |
| 5,128,015 A | 7/1992 | Szuminsky et al. |
| 5,141,868 A | 8/1992 | Shanks et al. |
| 5,151,166 A | 9/1992 | Harral et al. |
| 5,171,689 A | 12/1992 | Kawaguri et al. |
| 5,192,415 A | 3/1993 | Yoshioka et al. |
| 5,229,282 A | 7/1993 | Yoshioka et al. |
| 5,243,516 A | 9/1993 | White ................... 435/287.2 |
| 5,272,060 A | 12/1993 | Hamamoto et al. |
| 5,272,087 A | 12/1993 | El Murr et al. |
| 5,282,950 A | 2/1994 | Dietze et al. |
| 5,312,590 A | 5/1994 | Gunasingham et al. |
| 5,320,732 A | 6/1994 | Nankai et al. |
| 5,352,351 A | 10/1994 | White et al. |
| 5,382,346 A | 1/1995 | Uenoyama et al. |
| 5,384,028 A | 1/1995 | Ito et al. |
| 5,385,846 A | 1/1995 | Kuhn et al. |
| 5,388,163 A | 2/1995 | Elko et al. |
| 5,393,399 A | 2/1995 | Van den Berg et al. |
| 5,395,504 A | 3/1995 | Saurer et al. |
| 5,405,511 A | 4/1995 | White et al. |
| 5,413,690 A | 5/1995 | Kost et al. |
| 5,437,999 A | 8/1995 | Diebold et al. |
| 5,469,369 A | 11/1995 | Rose-Pehrsson et al. |
| 5,508,171 A | 4/1996 | Walling et al. |
| 5,508,203 A | 4/1996 | Fuller |
| 5,509,410 A | 4/1996 | Hill et al. |
| 5,520,787 A | 5/1996 | Hanagan et al. |
| 5,527,446 A | 6/1996 | Kosek et al. |
| 5,567,302 A | 10/1996 | Song et al. |
| 5,611,908 A | 3/1997 | Matthiessen et al. |
| 5,620,579 A | 4/1997 | Genshaw et al. |
| 5,628,890 A | 5/1997 | Carter et al. |
| 5,642,734 A | 7/1997 | Ruben |
| 5,645,709 A | 7/1997 | Birch et al. |
| 5,653,863 A | 8/1997 | Genshaw et al. |
| 5,660,791 A | 8/1997 | Brenneman et al. |
| 5,723,284 A | 3/1998 | Ye |
| 5,762,770 A | 6/1998 | Pritchard et al. |
| 5,849,174 A | 12/1998 | Sanghera et al. |
| 5,869,971 A | 2/1999 | Sherman |
| 5,909,114 A | 6/1999 | Uchiyama et al. |
| 5,942,102 A | 8/1999 | Hodges et al. |
| 5,997,817 A | 12/1999 | Crismore et al. |
| 6,058,934 A | 5/2000 | Sullivan |
| 6,071,391 A | 6/2000 | Gotoh et al. |
| 6,153,069 A | 11/2000 | Pottgen et al. |
| 6,179,979 B1 | 1/2001 | Hodges et al. |
| 6,193,873 B1 | 2/2001 | Ohara et al. |
| 6,251,260 B1 | 6/2001 | Heller et al. |
| 6,284,125 B1 | 9/2001 | Hodges et al. |
| 6,287,451 B1 | 9/2001 | Winarta et al. |
| 6,379,513 B1 | 4/2002 | Chambers et al. |
| 6,391,645 B1 | 5/2002 | Huang et al. |
| 6,413,410 B1 | 7/2002 | Hodges et al. |
| 6,461,496 B1 | 10/2002 | Feldman et al. |
| 6,475,372 B1 | 11/2002 | Ohara et al. |
| 6,503,381 B1 | 1/2003 | Gotoh et al. |
| 6,576,117 B1 | 6/2003 | Iketaki et al. |
| 6,595,919 B2 | 7/2003 | Berner et al. |
| 6,645,368 B1 | 11/2003 | Beaty et al. |
| 6,676,995 B2 | 1/2004 | Dick et al. |
| 6,730,200 B1 | 5/2004 | Stewart et al. |
| 6,749,887 B1 | 6/2004 | Dick et al. |
| 6,816,537 B2 | 11/2004 | Liess |
| 6,818,180 B2 | 11/2004 | Douglas et al. |
| 6,824,670 B2 | 11/2004 | Tokunaga et al. |
| 6,830,934 B1 | 12/2004 | Harding et al. |
| 6,863,801 B2 | 3/2005 | Hodges et al. |
| 6,869,411 B2 | 3/2005 | Langley et al. |
| 6,936,146 B2 | 8/2005 | Ryu et al. |
| 6,942,770 B2 | 9/2005 | Cai et al. |
| 7,008,525 B2 | 3/2006 | Morita et al. |
| 7,018,843 B2 | 3/2006 | Heller |
| 7,083,712 B2 | 8/2006 | Morita et al. |
| 7,122,111 B2 | 10/2006 | Tokunaga et al. |
| 7,132,041 B2 | 11/2006 | Deng et al. |
| 7,160,251 B2 | 1/2007 | Neel et al. |
| 7,201,042 B2 | 4/2007 | Yamaoka et al. |
| 7,338,639 B2 | 3/2008 | Burke et al. |
| 7,390,667 B2 | 6/2008 | Burke |
| 7,407,811 B2 | 8/2008 | Burke |
| 7,452,457 B2 | 11/2008 | Burke |
| 7,488,601 B2 | 2/2009 | Burke |
| 7,494,816 B2 | 2/2009 | Burke |
| 7,504,020 B2 | 3/2009 | Tokunaga et al. |
| 7,597,793 B2 | 10/2009 | Burke |
| 7,604,721 B2 | 10/2009 | Groll |
| 7,645,373 B2 | 1/2010 | Groll |
| 7,645,421 B2 | 1/2010 | Groll |
| 7,718,439 B2 | 5/2010 | Groll |
| 7,727,467 B2 | 6/2010 | Burke |
| 7,749,371 B2 | 7/2010 | Guo et al. |
| 7,749,437 B2 | 7/2010 | Mosoiu |
| 7,829,023 B2 | 11/2010 | Burke |
| 7,879,618 B2 | 2/2011 | Mosoiu |
| 7,892,849 B2 | 2/2011 | Burke |
| 7,923,258 B2 | 4/2011 | Heller |
| 7,927,882 B2 | 4/2011 | Heller |
| 7,955,492 B2 | 6/2011 | Fujiwara |
| 7,972,861 B2 | 7/2011 | Deng |
| 7,977,112 B2 | 7/2011 | Burke |
| 7,981,363 B2 | 7/2011 | Burke |
| 2002/0139692 A1 | 10/2002 | Tokunaga et al. |
| 2003/0036202 A1 | 2/2003 | Teodorcyzk et al. |
| 2003/0098233 A1 | 5/2003 | Kermani et al. |
| 2003/0109798 A1 | 6/2003 | Kermani |
| 2003/0203498 A1* | 10/2003 | Neel ............. C12Q 1/006 436/95 |
| 2004/0005716 A9 | 1/2004 | Beaty |

(56) References Cited

U.S. PATENT DOCUMENTS

| | | |
|---|---|---|
| 2004/0079652 A1 | 4/2004 | Vreeke et al. |
| 2004/0120848 A1 | 6/2004 | Teodorczyk |
| 2004/0154932 A1 | 8/2004 | Deng et al. |
| 2004/0182703 A1 | 9/2004 | Bell et al. |
| 2004/0219624 A1 | 11/2004 | Teodorcyzk et al. |
| 2004/0235178 A1 | 11/2004 | Tokunaga et al. |
| 2004/0256248 A1 | 12/2004 | Burke et al. |
| 2004/0260511 A1 | 12/2004 | Burke et al. |
| 2005/0036906 A1 | 2/2005 | Nakahara |
| 2005/0045476 A1 | 3/2005 | Neel et al. |
| 2005/0153457 A1 | 7/2005 | Patel et al. |
| 2005/0247562 A1 | 11/2005 | Tokunaga et al. |
| 2005/0258034 A1* | 11/2005 | Iketaki ............... G01N 27/3274 204/403.01 |
| 2005/0284758 A1 | 12/2005 | Funke |
| 2006/0108236 A1 | 5/2006 | Kasielke et al. |
| 2006/0231418 A1 | 10/2006 | Harding et al. |
| 2006/0231421 A1 | 10/2006 | Diamond et al. |
| 2006/0231423 A1 | 10/2006 | Harding et al. |
| 2006/0231425 A1 | 10/2006 | Harding et al. |
| 2007/0000777 A1 | 1/2007 | Ho et al. |
| 2007/0017824 A1 | 1/2007 | Rippeth et al. |
| 2007/0074977 A1 | 4/2007 | Guo et al. |
| 2007/0102292 A1 | 5/2007 | Dreibholz et al. ............ 204/401 |
| 2007/0227912 A1 | 10/2007 | Chatelier et al. |
| 2007/0235346 A1 | 10/2007 | Popovich et al. |
| 2007/0235347 A1 | 10/2007 | Chatelier et al. |
| 2007/0256943 A1 | 11/2007 | Popovich |
| 2008/0083618 A1 | 4/2008 | Neel et al. |
| 2009/0014339 A1 | 1/2009 | Beer et al. |
| 2009/0084687 A1 | 4/2009 | Chatelier et al. |
| 2009/0099787 A1 | 4/2009 | Carpenter |
| 2009/0184004 A1 | 7/2009 | Chatelier |
| 2009/0205976 A1* | 8/2009 | Yoshioka ........... G01N 27/3274 205/775 |
| 2009/0301899 A1 | 12/2009 | Hodges et al. |
| 2010/0089775 A1 | 4/2010 | Chen |
| 2010/0170807 A1 | 7/2010 | Diebold |
| 2010/0206749 A1 | 8/2010 | Choi |
| 2010/0276303 A1 | 11/2010 | Fujiwara |
| 2011/0011752 A1 | 1/2011 | Chatelier et al. |
| 2011/0297554 A1 | 12/2011 | Wu |
| 2011/0301857 A1 | 12/2011 | Huang |

FOREIGN PATENT DOCUMENTS

| | | |
|---|---|---|
| AU | 2007201377 | 8/2009 |
| AU | 2009200097 | 1/2011 |
| AU | 2009202200 | 1/2011 |
| CA | 2748433 | 9/2007 |
| CA | 2582643 | 10/2011 |
| CN | 1338049 A | 2/2002 |
| CN | 1692277 A | 11/2005 |
| DE | 3103464 | 8/1982 |
| EP | 0171375 A1 | 2/1986 |
| EP | 0172969 A2 | 3/1986 |
| EP | 0251915 | 1/1988 |
| EP | 0255291 A1 | 2/1988 |
| EP | 0266204 | 5/1988 |
| EP | 0278647 | 8/1988 |
| EP | 0290770 A2 | 11/1988 |
| EP | 0299779 | 1/1989 |
| EP | 0351516 | 1/1990 |
| EP | 0351891 A2 | 1/1990 |
| EP | 0351892 A2 | 1/1990 |
| EP | 0359831 A1 | 3/1990 |
| EP | 0400918 | 12/1990 |
| EP | 0418404 | 3/1991 |
| EP | 0451981 A2 | 10/1991 |
| EP | 0560336 A1 | 9/1993 |
| EP | 0800086 A1 | 10/1997 |
| EP | 1 042 667 A1 | 10/2000 |
| EP | 1 081 490 A1 | 3/2001 |
| EP | 1 156 324 A1 | 11/2001 |
| EP | 1156324 A1 | 11/2001 |
| EP | 1172649 A1 | 1/2002 |
| EP | 1 281 960 A2 | 2/2003 |
| EP | 1281960 A2 | 2/2003 |
| EP | 1 394 545 A1 | 3/2004 |
| EP | 1447452 A1 | 8/2004 |
| EP | 1 455 182 A1 | 9/2004 |
| EP | 1557662 A1 | 7/2005 |
| EP | 1 775 587 A2 | 4/2007 |
| EP | 1 840 219 A1 | 10/2007 |
| EP | 1839571 A1 | 10/2007 |
| EP | 1839571 A1 | 10/2007 |
| EP | 1840219 A1 | 10/2007 |
| EP | 1840219 A1 | 10/2007 |
| EP | 2098857 | 12/2009 |
| EP | 2267149 | 12/2010 |
| EP | 2076168 | 1/2012 |
| EP | 2 482 069 A1 | 8/2012 |
| GB | 2020424 | 11/1979 |
| GB | 2154735 | 9/1985 |
| GB | 2201248 | 8/1988 |
| GB | 2235050 | 2/1991 |
| JP | 3099254 | 4/1991 |
| JP | 3167464 | 7/1991 |
| JP | 4066112 | 3/1992 |
| JP | 4343065 A | 11/1992 |
| JP | 5002007 A | 1/1993 |
| JP | 6222874 | 8/1994 |
| JP | 11230934 A | 8/1999 |
| JP | 2001-066274 A | 3/2001 |
| JP | 200166274 | 3/2001 |
| JP | 2001153839 A | 6/2001 |
| JP | 2003114214 A | 4/2003 |
| JP | 2003-185615 | 7/2003 |
| JP | 2003521708 A | 7/2003 |
| JP | 2003240747 | 8/2003 |
| JP | 2003-262604 | 9/2003 |
| JP | 2004245836 A | 9/2004 |
| JP | 2005147990 A | 6/2005 |
| JP | 2005-523443 A | 8/2005 |
| JP | 2007087710 | 4/2007 |
| JP | 2007108171 A | 4/2007 |
| JP | 2007133985 | 5/2007 |
| JP | 2007522449 | 8/2007 |
| JP | 2007225619 | 9/2007 |
| JP | 2007248281 | 9/2007 |
| JP | 2007-271622 | 10/2007 |
| JP | 2007271623 | 10/2007 |
| JP | 2007531877 | 11/2007 |
| JP | 2009528540 | 8/2009 |
| JP | 2009-536744 A | 10/2009 |
| SU | 1351627 | 11/1987 |
| WO | WO-8908713 A1 | 9/1989 |
| WO | WO 91/09373 | 6/1991 |
| WO | WO-9215701 A1 | 9/1992 |
| WO | WO-9402842 A1 | 2/1994 |
| WO | WO-9516198 A1 | 6/1995 |
| WO | WO-9700441 A1 | 1/1997 |
| WO | WO-9718465 A1 | 5/1997 |
| WO | WO-0020626 A1 | 4/2000 |
| WO | 01/40787 A1 | 6/2001 |
| WO | 0157510 A2 | 8/2001 |
| WO | WO 01/57510 A2 | 8/2001 |
| WO | WO-0157510 A2 | 8/2001 |
| WO | WO 03/089658 A1 | 10/2003 |
| WO | 2004040286 A1 | 5/2004 |
| WO | WO2004113913 | 12/2004 |
| WO | WO 2005/008231 A1 | 1/2005 |
| WO | WO2005066355 | 7/2005 |
| WO | 2005098424 A1 | 10/2005 |
| WO | WO 2006/109280 A2 | 10/2006 |
| WO | WO 2006/110504 A1 | 10/2006 |
| WO | WO-2006110504 A1 | 10/2006 |
| WO | WO 2007/040913 A1 | 4/2007 |
| WO | WO2006109277 | 4/2007 |
| WO | 2007/133985 A2 | 11/2007 |
| WO | 2007130907 A2 | 11/2007 |

(56) References Cited

FOREIGN PATENT DOCUMENTS

| | | |
|---|---|---|
| WO | WO 2007/131036 A1 | 11/2007 |
| WO | WO 2008/004565 A1 | 1/2008 |

OTHER PUBLICATIONS

Australian Patent Examination Report for AU 2013263734; Dated: Mar. 25, 2015; 4 pages.
Singapore Search Report and Written Opinion for SG 2013028881; Dated: Nov. 21, 2014 and Mar. 11, 2015; 21 pages.
Australian Patent Examination Report for AU 2015203087; dated: Jul. 12, 2016; 9 pages.
Japanese Office Action for JP 2012-261693; dated: Mar. 24, 2015; 2 pages.
Canadian Office Action ad Examination Search Report for CA 2,648,625; dated: Apr. 7, 2015; 5 pages.
Singapore Examination Report for SG 2013028881; dated: Apr. 11, 2016; 11 pages.
Chinese Office Action and Search Report for CN 201310139029.3; dated Sep. 3, 2014; 10 pages.
Japanese Office Action for JP 2012-261693; dated Sep. 2, 2014; 2 pages.
Canadian Office Action for CA 2,668,237; dated Jun. 4, 2014 (3 pages).
Indian Examination Report for IN 1627/KOL/2008; dated Mar. 27, 2013 (2 pages).
Australian Patent Examination Report for AU 2013202708; dated Feb. 18, 2014 (6 pages).
Australian Patent Examination Report for AU 2013202716; dated Feb. 28, 2014 (3 pages).
Australian Patent Examination Report for AU 2013202702; dated Mar. 11, 2014 (6 pages).
Japanese Office Action for JP 2013-129601; dated Mar. 11, 2014 (2 pages).
Chinese Office Action for CN 200810175601.0; dated Nov. 28, 2013 (6 pages).
Japanese Office Action for JP 2012-261693; dated Feb. 12, 2014 (5 pages).
Canadian Office Action for 2,748,433; dated Aug. 1, 2013; 3 pages.
AU Examination Report for 2012201914; dated Sep. 6, 2013; 2 pgs.
AU Examination Report for 2012201915; dated Sep. 6, 2013; 2 pgs.
Chinese Office Action and Search Report for CN 200810175601.0; dated Mar. 20, 2013 and Mar. 11, 2013; 7 pages.
EP Examination Report for EP 09 250 133.7; dated May 16, 2013; 4 pages.
EP Examination Report for EP 12 164 561.8; dated May 2, 2013; 2 pages.
AU Examination Report for 2009227823; dated Nov. 1, 2012; 3 pages.
AU Examination Report for 2012201912; dated Jan. 11, 2013; 4 pages.
AU Examination Report for 2012201916; dated Jan. 24, 2013; 4 pages.
AU Examination Report for 2009227823; dated Feb. 18, 2013; 3 pages.
EP Office Action for 09251507.1; dated Sep. 13, 2012; 4 pages.
JP Office Action for 2012-261693; dated Feb. 5, 2013; 2 pages.
SG Examination Report for 200900312-0; dated Oct. 11, 2012; 9 pages.
EP report for 12164561 dated Jul. 4, 2012.
Schmidt, "New Principles of amperometric enzyme electrodes . . . " Sensors and Actuators B; vol. 13, No. 1-3, May 1, 1993.
EP report for 12173292 dated Sep. 12, 2012.
EP report for 12173297 dated Sep. 14, 2012.
EP report for 12173284 dated Sep. 7, 2012.
JP report for 2012076986 dated Sep. 4, 2012.
Cha, Kichul, et al., An electronic method for rapid measurement of haematocrit in blood samples; Physiol Meas, 1994.
CN report for 200910134602 dated Aug. 17, 2012.
JP report for 2009137856 dated Jul. 31, 2012.
Wikipedia: "Hematocrit"; http://en.wikipedia.org/w/index.php?title=Hematocrit&printable=yes; Retrieved on May 24, 2012; 3 pages.
European Search Report for EP Application No. 08 253 148.4; mailed Jun. 4, 2012; 3 pages.
European Search Retort for EP Application No. 07 251 388.0; mailed Jun. 5, 2012; 3 pages.
European Search Report for EP Application No. 10 178 982.4; mailed Jun. 5, 2012; 2 pages.
European Search Report for EP Application No. 10 178 905.5; mailed Jun. 8, 2012; 4 pages.
Chinese Office Action issued Nov. 22, 2011 for Application No. 200910134602.5 (15 Pages).
Japanese Office Action issued Nov. 29, 2011 for Application No. 2009-006871 (3 Pages).
Japanese Office Action issued Jan. 10, 2012 for Application No. 2011-123761 (3 Pages).
Numerical Recipes: The Art of Scientific Computing, Third Edition. William H. Press et al., Cambridge University Press, Published 2007.
European Extended Search Report for Application No. EP 09250133, dated Nov. 30, 2009, 10 pages.
European Extended Search Report for Application No. EP 09251507, dated Sep. 14, 2011, 11 pages.
European Extended Search Report for Application No. 07251388.0, dated Jul. 9, 2007, 6 pages.
Canadian Examiner's Requisition for Application No. 2648625, dated Apr. 11, 2011, 3 pages.
Japanese Office Action for Application No. JP 2007-087710, mailed Aug. 9, 2011, 2 pages.
European Search Report, Application No. EP 09251507, mailed May 11, 2011, 5 pages.
Australian Examiner's Report for application No. 2007201377 dated Mar. 19, 2009, 3 pages.
Canadian Examiner's Requisition for application No. 2582643 dated May 19, 2009, 4 pages.
Canadian Examiner's Requisition for application No. 2582643 dated Mar. 10, 2010, 4 pages.
European Examination Report for application No. 07251388.0 dated Apr. 10, 1008, 4 pages.
Australian Examiner's Report for application No. 2008221593 dated Mar. 30, 3011, 3 pages.
Canadian Examiner's Requisition for application No. 2639776 dated Dec. 21, 2010, 6 pages.
Australian Examiner's Report for application No. 2009200097 dated Jul. 2, 2010, 2 pages.
Australian Examiner's Report for application No. 2011201199 dated May 10, 2011, 2 pages.
European Search Report , Application No. EP 10178982 mailed Nov. 22, 2010.
Japanese Office Action, Application No. JP 2009-006871 mailed Mar. 1, 2011.
European Search Report , Application No. EP 08253148.4 mailed Nov. 24, 2010.
European Search Report , Application No. EP 10178905, dated Nov. 25, 2010, 7 pages.
Australian Search Report for Australian application No. 2008221593, dated Mar. 29, 2010, 3 pages.
Australian Examiner's first report on Patent Application No. 2009202200, dated Jul. 22, 2010 (3 pages).
(Abstract Only) Kobayashi Yoshiaki et al., Biosensor, JP 61002060, Jan. 8, 1986., </TD></TR>.
Laszlo Daruhazi et al. "Cyclic Voltammetry for Reversible Redox-Electrode Reactions in Thin-Layer Cells With Closely Separated Working and Auxiliary Electrodes of the Same Size" in J. Electroanal. Chem., 264:77-89 (1989).
Osamu, Niwa, et al., "Electrochemical Behavior of Redox Species at Interdigitated Array Electrodes with Different Geometries: Consideration of Redox Cycling and Collection Efficiency," Analytical Chemistry; Mar. 1990, vol. 62, No. 5, pp. 447-452.

(56) References Cited

OTHER PUBLICATIONS

European Search Report, Application No. EP 09250133, Mailed Sep. 15, 2009.
Australian Examiner's first report on Patent Application No. 2007201377, dated Jun. 25, 2008.
Indian Examination Report for IN 86/KOL/2009; dated: Jan. 29, 2016; 2 pages.
Japanese Office Action for JP 2015-025466; dated Mar. 1, 2016; 3 pages.
Singapore Written Opinion for SG 2013028881; dated: Nov. 6, 2015; 11 pages.
Japanese Office Action for JP 2015-025466; dated: Jul. 5, 2016; 1page.
Australian Examination Report for AU 2015203087; dated: Jan. 25, 2017; 2pages.
Japanese Office Action for JP 2015-025466; dated: Mar. 7, 2017; 2 pages.
Canadian Office Action and Examination Report for CA 2,934,333; dated: Mar. 31, 2017; 3 pages.
European Search Report for EP 17 156 437.0; dated: May 5, 2017; 8 pages.

\* cited by examiner

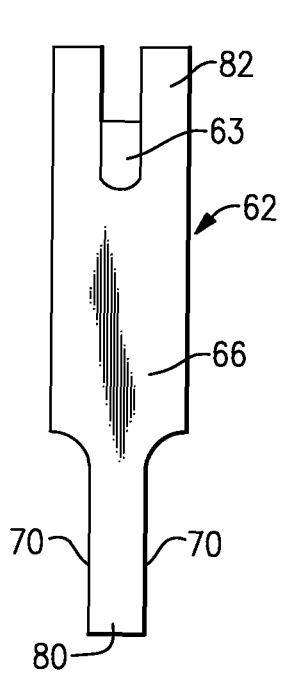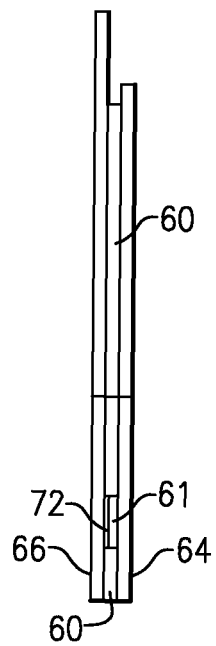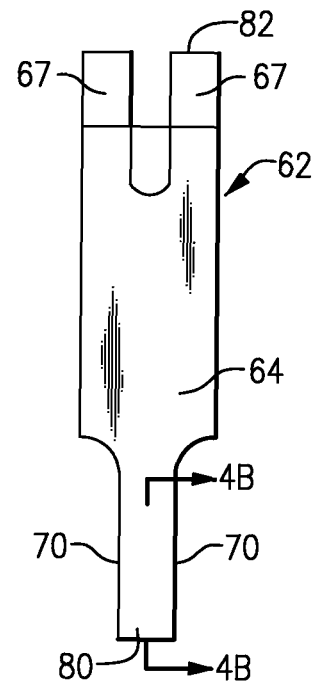
FIG.2    FIG.3    FIG.4A
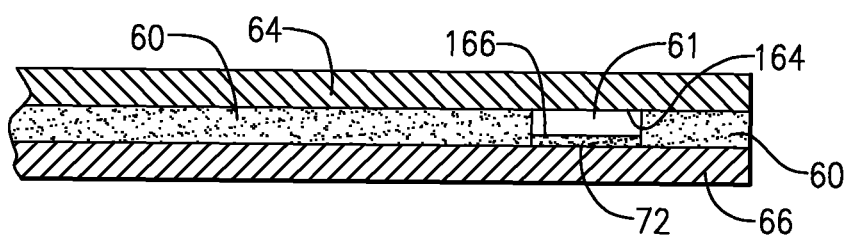
FIG.4B

SYSTEM AND METHOD FOR MEASURING AN ANALYTE IN A SAMPLE

CROSS REFERENCE TO RELATED APPLICATIONS

This application is a continuation application of U.S. patent application Ser. No. 13/619,463, entitled: "System and Method for Measuring an Analyte in a Sample", filed Sep. 14, 2012, which is a divisional patent application of U.S. patent application Ser. No. 12/349,017, entitled: "Systems and Method for Measuring an Analyte", filed on Jan. 6, 2009, which claims priority pursuant to 35 U.S.C. §119 to U.S. Provisional Patent Application Ser. No. 61/021,713, entitled "System and Method For Measuring An Analyte In A Sample," filed on Jan. 17, 2008, the entirety of each of these applications being incorporated herein by reference.

FIELD

The present disclosure relates to methods and systems for determining analyte concentration of a sample.

BACKGROUND

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management of a variety of disease conditions. Analytes of interest include glucose for diabetes management, cholesterol, and the like. In response to this growing importance of analyte detection, a variety of analyte detection protocols and devices for both clinical and home use have been developed.

One type of method that is employed for analyte detection is an electrochemical method. In such methods, an aqueous liquid sample is placed into a sample-receiving chamber in an electrochemical cell that includes at least two electrodes, e.g., a counter electrode and a working electrode. The analyte is allowed to react with a redox reagent to form an oxidizable (or reducible) substance in an amount corresponding to the analyte concentration. The quantity of the oxidizable (or reducible) substance present is then estimated electrochemically and related to the amount of analyte present in the initial sample.

Such systems are susceptible to various modes of inefficiency and/or error. For example, where the physiological sample being assayed is whole blood or a derivative thereof, the hematocrit of the sample can be a source of analytical error in the ultimate analyte concentration measurement. Thus, in electrochemical measurement protocols where the analyte concentration is derived from observed time-current transients, increased hematocrit levels can increase the sample viscosity, which in turn, can slow the diffusion of enzyme, analyte, and mediator, thereby attenuating the test current and causing analytical error. Additionally, a partial fill or a double-fill of a sample-receiving chamber, a defective test strip, and/or leakage of sample can result in incorrect and/or inefficient testing.

SUMMARY OF THE INVENTION

Various aspects of a method of calculating a corrected analyte concentration of a sample are provided. That is, the methods typically include making an initial analyte determination, determining a correction factor based on various system measurements and/or parameters, and modifying the initial analyte concentration based on the correction factor thereby overcoming some source of error. For example, the analyte can be glucose and the error source can be an increased hematocrit level which if not accounted for could result in an incorrect reading. Other methods account for various system errors such as double-dosing events, maximum current check, minimum current check, high resistance track, and/or leakage. While the methods provided below are focused on the detection of glucose, various other protocols are within the spirit and scope of the disclosure. For example, the method can be utilized for the detection or measurement of lactate, cholesterol, hemoglobin or total antioxidants.

In use, the methods are performed with an electrochemical cell which is sized and configured to receive a sample (e.g., blood). The electrochemical cell typically includes at least two electrodes configured so that they are closely spaced and can be wetted by a small volume of liquid. The various methods are capable of determining an accurate analyte concentration in view of some error source or determining some system error by determining various current readings during one or many applied voltages, determining a correction factor from the various readings, and using this correction factor to determine a corrected analyte concentration. The electrochemical cell is used in conjunction with a meter. An electrical power source, for example a battery, in the meter is used to apply a voltage or a series of voltages across the electrodes of the electrochemical cell thereby causing an electrical current to flow. The current flowing is measured by electronic circuitry in the meter as a function of time and the current measurements can be used to derive a concentration of the analyte of interest.

The methods provided herein typically involve applying various test voltages for certain pre-determined time periods, measuring test currents present during those time periods, and utilizing these measurements to determine an initial analyte concentration, a correction factor, an error source, and a corrected analyte concentration. For example, the method can include providing a sample (e.g., blood) with an unknown glucose concentration to an electrochemical cell and applying a first test voltage $V_1$ for a first time interval $T_1$ between a first electrode and a second electrode sufficient to oxidize a reduced mediator at the second electrode. Additionally, the method can include applying a second test voltage $V_2$ for a second time interval $T_2$ between the first electrode and the second electrode sufficient to oxidize the reduced mediator at the first electrode where the first test voltage $V_1$ is applied before the second test voltage $V_2$. In this example, the method can include calculating a initial glucose concentration $G_1$ based on test current values during the first time interval $T_1$ and the second time interval $T_2$, calculating an error source, in this case an increased hematocrit level H, and calculating a corrected glucose concentration $G_2$ based on the initial glucose concentration $G_1$ and the hematocrit level H.

In one embodiment, the step of calculating the corrected glucose concentration includes calculating a correction value Corr with a first function if the hematocrit level H is less than a lower predetermined hematocrit level $H_L$ (e.g., about 30%) and if the initial glucose concentration $G_1$ is less than an upper predetermined glucose concentration $G_U$ (e.g., about 300 mg/dL). For example, the first function can be an equation Corr=$K_1(H_L-H) G_1$ where Corr is the correction value, $K_1$ is a first constant (e.g., about −0.004), $H_L$ is the lower predetermined hematocrit level (e.g., about 30%), H is the hematocrit level, and $G_1$ is the initial glucose concentration. The various constants in the equations are typically derived empirically, where a set of test results are obtained with the measurement system using whole blood with different hematocrit and glucose concentrations spanning the range of interest. Typically, nonlinear least squares fitting procedure is then used, where the constants that give the smallest overall difference between the value of the parameter of interest derived from the current data, and the actual value of the parameter are determined. The parameter of interest depends at least in part on the constants being determined. For example, if the constants formed part of an equation which estimated the hematocrit of the sample, then the sample hematocrit would be the parameter of interest. In the case of the constants in the equation for Corr given above, the parameter of interest is the concentration of glucose in the blood. Those skilled in the art will appreciate that various other statistical analysis methods can be utilized to provide values for the constants.

The correction factor can be determined if the hematocrit level and the initial glucose concentration fall within other ranges. For example, the step of calculating the second glucose concentration includes calculating a correction value Corr with a second function if the hematocrit H is less than a lower predetermined hematocrit level $H_L$ (e.g., about 30%) and if the initial glucose concentration $G_1$ is greater than the upper predetermined glucose concentration $G_U$ (e.g., about 300 mg/dL). In such an embodiment, the method can also include calculating a corrected glucose concentration $G_2$ based on the initial glucose concentration $G_1$, the hematocrit level H, and the correction value Corr. Additionally, the second function can be an equation such as Corr=$K_2$ ($H_L$−H) ($G_{max}$−$G_1$) where Corr is the correction value, $K_2$ is a second constant (e.g., −0.004), $H_L$ is the lower predetermined hematocrit level (e.g., about 30%), H is the hematocrit level, $G_{max}$ is a predetermined maximum glucose concentration (e.g., about 600 mg/dL), and $G_1$ is the first glucose concentration.

In certain circumstances, the method can also assign and utilize a correction value Corr equal to zero. For example, in one embodiment, the corrected glucose concentration $G_2$ can be substantially equal to the initial glucose concentration $G_1$ (i.e., Corr=0) if the hematocrit level H is greater than an upper predetermined hematocrit level $H_U$ (e.g., about 50%) and if the initial glucose concentration $G_1$ is less than a lower predetermined glucose concentration $G_L$ (e.g., about 100 mg/dL) or the hematocrit level H is less than an upper predetermined hematocrit level $H_U$ (e.g., about 50%) and greater than a lower predetermined hematocrit level $H_L$ (e.g., about 30%).

In one embodiment, the step of calculating the second glucose concentration $G_2$ includes calculating a correction value Corr with a fourth function if the hematocrit level H is greater than an upper predetermined hematocrit level $H_U$ (e.g., about 50%) and if the initial glucose concentration $G_1$ is greater than the lower predetermined glucose concentration $G_L$ (e.g., about 100 mg/dL). In such an embodiment, the method can also include calculating a corrected glucose concentration $G_2$ based on the initial glucose concentration $G_1$, the hematocrit level H, and the correction value Corr. Additionally, the fourth function can be an equation such as Corr=$K_4$(H−$H_U$) ($G_1$−$G_L$) where Corr equals the correction value, $K_4$ is a fourth constant (e.g., 0.011), H is the hematocrit level, $H_U$ is the upper predetermined hematocrit level (e.g., about 50%), $G_1$ is the initial glucose concentration, and $G_L$ is the lower predetermined glucose concentration (e.g., about 100 mg/dL).

Various correction equations can be utilized to find a value for the corrected glucose concentration $G_2$. For example, in some embodiments, the correction equation can be selected based on the initial glucose concentration relative to some glucose threshold. That is, the method can include the step of calculating the corrected glucose concentration $G_2$ using a correction equation in those cases where the initial glucose concentration $G_1$ is less than a glucose threshold with the correction equation being $G_2$=$G_1$+Corr. Also, the method can include the step of calculating the corrected glucose concentration $G_2$ using a correction equation if the initial glucose concentration $G_1$ is greater than a glucose threshold wherein this correction equation is $$G_2 = G_1\left(1 + \frac{\text{Corr}}{100}\right).$$

As will be apparent to those skilled in the art, any number and magnitude of test voltages can be supplied to the sample at any number or pattern of time intervals. For example, in one embodiment, the second test voltage $V_2$ can be applied immediately after the first test voltage $V_1$. Also, the first test voltage $V_1$ can have a first polarity and the second test voltage $V_2$ has a second polarity wherein the first polarity is opposite in magnitude or sign to the second polarity. As indicated, the first and second test voltage can be of virtually any amount capable of providing the desired effect. For example, in one embodiment, the first test voltage $V_1$ can range from about −100 mV to about −600 mV with respect to the second electrode, and the second test voltage $V_2$ can range from about +100 mV to about +600 mV with respect to the second electrode. Additionally, the method can further include applying a third test voltage $V_3$ for a third time interval $T_3$ between the first electrode and the second electrode where the absolute magnitude of the resulting test current is substantially less than the absolute magnitude of the resulting test current for the second test voltage $V_2$. The third test voltage can be applied before the first test voltage $V_1$ or at any other time interval (e.g., after the second test voltage) as desired. Additionally, various arrangement and/or configurations of electrodes are included herein. For example, in an exemplary embodiment, the first electrode and the second electrode can have an opposing face arrangement. Additionally, a reagent layer can be disposed on the first electrode.

The method also provides various manners of measuring a patient's hematocrit level. For example, the hematocrit level H can be based on test current values during the first time interval $T_1$ and the second time interval $T_2$. In an exemplary embodiment, the hematocrit level H can be calculated using a hematocrit equation. For example, the hematocrit equation can be H=$K_5$ ln(|$i_2$|)+$K_6$ ln($G_1$)+$K_7$ where H is the hematocrit level, $K_5$ is a fifth constant (e.g., −76.001), $i_2$ is at least one current value during the second time interval, $K_6$ is a sixth constant (e.g., 56.024), $G_1$ is the initial glucose concentration, and $K_7$ is a seventh constant (e.g., 250).

In another aspect, a method of calculating an analyte concentration is provided which includes applying a first test voltage $V_1$ for a first time interval $T_1$ between a first electrode and a second electrode sufficient to oxidize a reduced mediator at the second electrode, and applying a second test voltage $V_2$ for a second time interval $T_2$ between the first electrode and the second electrode sufficient to oxidize the reduced mediator at the first electrode. The method also includes calculating an initial glucose concentration $G_1$ based on test current values during the first time interval $T_1$ and the second time interval $T_2$. The method further includes calculating a hematocrit level H, and applying a first function to calculate the corrected glucose concentration if the initial glucose concentration $G_1$ is less than an upper predetermined glucose concentration $G_U$ and the hematocrit level is less than a lower predetermined hematocrit level $H_L$. The method also includes applying a second function to calculate the corrected glucose concentration if the initial glucose concentration $G_1$ is greater than an upper predetermined glucose concentration $G_U$ and the hematocrit level is less than a lower predetermined hematocrit level $H_L$, applying a third function to calculate the corrected glucose concentration if the initial glucose concentration $G_1$ is less than a lower predetermined glucose concentration $G_L$ and the hematocrit level is greater than an upper predetermined hematocrit level $H_U$, and applying a fourth function to calculate the corrected glucose concentration if the initial glucose concentration $G_1$ is greater than a lower predetermined glucose concentration $G_L$ and the hematocrit level is greater than an upper predetermined hematocrit level $H_U$.

The various functions can include various equations. For example, the first function can include an equation such as $Corr = K_1(H_L - H) G_1$ where Corr is the correction value, $K_1$ is a first constant (e.g., −0.004), $H_L$ is the lower predetermined hematocrit level (e.g., about 30%), H is the hematocrit level, and $G_1$ is the initial glucose concentration. The second function can include an equation such as $Corr = K_2(H_L - H)(G_{max} - G_1)$ where Corr is the correction value, $K_2$ is a second constant (e.g., −0.004), $H_L$ is the lower predetermined hematocrit level (e.g., about 30%), H is the hematocrit level, $G_{max}$ is a predetermined maximum glucose concentration (e.g., about 600 mg/dL), and $G_1$ is the initial glucose concentration. The third function can includes an equation such as $Corr = 0$ where Corr is the correction value, and the fourth function can include an equation such as $Corr = K_4(H - H_U)(G_1 - G_L)$ where Corr is the correction value, $K_4$ is a fourth constant (e.g., 0.011), H is the hematocrit level, $H_U$ is the upper predetermined hematocrit level (e.g., about 50%), $G_1$ is the initial glucose concentration, $G_L$ is the lower predetermined glucose concentration (e.g., about 100 mg/dL).

Additionally, the various correction values can be utilized with various embodiments of a correction equation configured to provide an adjusted analyte value. For example, the method can include the step of calculating the corrected glucose concentration $G_2$ with a correction equation if the initial glucose concentration $G_1$ is less than a glucose threshold wherein the correction equation is $G_2 = G_1 + Corr$. The method can also include the step of calculating the corrected glucose concentration $G_2$ with a correction equation if the initial glucose concentration $G_1$ is greater than a glucose threshold, the correction equation being $$G_2 = G_1 \left(1 + \frac{Corr}{100}\right).$$

In one embodiment, the method can also include applying a third test voltage $V_3$ for a third time interval $T_3$ between the first electrode and the second electrode where the absolute magnitude of the resulting test current is substantially less than the absolute magnitude of the resulting test current for the second test voltage $V_2$. In such an embodiment, the third test voltage $V_3$ can be applied before the first test voltage $V_1$. In such an embodiment, the third test voltage $V_3$ is of a magnitude that results in a test current that is substantially less than the absolute magnitude of the resulting test current for the second test voltage $V_2$ to minimize interference with the currents that are measured during the application of $V_1$ and $V_2$. The smaller current flowing during the application of $V_3$ means a smaller amount of redox species is electrochemically reacted at the electrodes so less disruption of the concentration profiles of the redox species in the electrochemical cell will be caused by the application of $V_3$.

Various embodiments of a method of identifying a defect (e.g., high track resistance) in a test strip are also provided. In one such aspect, a method is provided which includes applying a first test voltage for a first test time interval between a first electrode and a second electrode sufficient to oxidize a reduced mediator at the second electrode, and applying a second test voltage for a second test time interval between a first electrode and a second electrode sufficient to oxidize a reduced mediator at the first electrode. Alternatively, only a first test voltage applied for a first time interval is required to practice the method. The method can also include measuring a first test current and a second test current that occur during the first or second test time interval wherein the second test current occurs after the first test current during the same test time interval, and determining whether the test strip has the defect using an equation based on the first test current, and the second test current. In an exemplary embodiment, the second test voltage can be applied immediately after the first test voltage.

Various embodiments of such an equation are provided herein. For example, the equation can include a ratio between the first test current and the second test current. Additionally, the equation can include a ratio between the first test current and the difference between the first test current and the second test current. In one embodiment, the first test current can occur at about a beginning of the first or second test time interval, and the first test current can be a maximum current value occurring during the first or second test time interval. Also, the second test current can occur at about an end of the first or second test time interval, and the second test current is a minimum current value occurring during the first or second test time interval. In one example, the equation can be a $$ratio = \frac{i_1}{i_1 - i_2},$$

where $i_1$ is me first test current and $i_2$ is the second test current. In use, the method can include a step of providing an error message indicating a defective test strip if the ratio is greater than a first predetermined threshold (e.g., about 1.2).

Similar to above, various arrangements and/or configurations of electrodes are included within the spirit and scope of the present disclosure. For example, a polarity of the first test voltage is opposite to a polarity of the second test voltage. Also, the first electrode and second electrode have an opposing face arrangement. Additionally, the first voltage and/or the second voltage can be any of a wide range of voltages. For example, the first test voltage can range from about zero to about −600 mV with respect to the second electrode, and the second test voltage can range from about 10 mV to about 600 mV with respect to the second electrode.

As indicated, one such defect to be identified by an embodiment of the method can be a high track resistance. For example the high track resistance can be between an electrode connector and the electrodes in the electrochemical cell. The function of the tracks is to provide an electrically conductive path between the connection points on the meter and the electrodes in the electrochemical cell. While current is flowing down these tracks some of the voltage applied by the meter will be dissipated along the tracks according to Ohm's Law, with the higher the electrical resistance and current flow down the track the greater the voltage drop. In this embodiment, the method is based upon the current flowing between the electrodes at short times after the application of a voltage being larger than the current flowing at longer times, due to the initially higher concentration of reduced mediator close to the electrode at short times. If the track resistance is too high, while current is flowing the voltage drop that occurs along the tracks will be greater than desired when the larger initial currents are attempting to flow. This larger than desired voltage drop will result in insufficient voltage being applied between the electrodes in the electrochemical cell, which in turn will cause a lower current to flow than would be the case if there was acceptable track resistance. According to this embodiment, the lower than expected current flowing at short times is detected by comparing it by the methods disclosed above to the current flowing at longer times, which naturally being lower is not so affected by the high track resistance.

In another aspect, a method of identifying a defect (e.g., leakage) in a test strip is provided. Such methods can include applying a first test voltage for a first test time interval between a first electrode and a second electrode sufficient to oxidize a reduced mediator at the second electrode, and applying a second test voltage for a second test time interval between a first electrode and a second electrode sufficient to oxidize a reduced mediator at the first electrode. The method also includes measuring a first test current, a second test current, a third test current, and a fourth test current that occur during the second test time interval, calculating a first logarithm of a first ratio based on the first test current and the second test current, calculating a second logarithm of a second ratio based on the third test current and the fourth test current, and determining whether the test strip has a defect using an equation based on the first logarithm and the second logarithm. In an exemplary embodiment, the defect is a leakage of fluid between a spacer and the first electrode. In some embodiments, a reagent layer can be disposed on the first electrode so that a portion of the reagent layer can be between the spacer and the first electrode.

Similar to above, various such equations are provided. In an exemplary embodiment, the equation is a third ratio represented by $$\frac{\log\left(\frac{i_1}{i_2}\right)}{\log\left(\frac{i_3}{i_4}\right)},$$

where $i_1$ is the first test current $i_2$, is the second test current, $i_3$ is the third test current, and $i_4$ is the fourth test current. In use, the method can further include a step of providing an error message indicating a defective test strip if the third ratio is less than a predetermined threshold (e.g., about 1, about 0.95, etc.).

In one embodiment, the first test current and the second test current can be the two largest current values during the second time interval. In one embodiment, the fourth test current can be a smallest current value occurring during the second time interval. Also, in one embodiment, a difference between a fourth test current time and a third test current time is greater than a difference between a second test current time and a first test current time. In this embodiment, the method includes comparing the shape of the current versus time profile, as embodied by the $i_1$, $i_2$, $i_3$, and $i_4$ measured currents, to an expected shape, as embodied by the predetermined threshold, in order to make a judgment or determination as to whether the shape of the current transient is acceptable.

Additionally, various aspects of a method of identifying an error in performing a test with a test strip are provided herein. In one such aspect, the method includes applying a test voltage for a test time interval between a first electrode and a second electrode, measuring consecutively a first test current, a second test current, and a third test current, and determining whether an error was performed by using an equation based on the second test current and a summation of the absolute value of the first test current and the absolute value of the third test current. Various time differences between measurements can be utilized. For example, a time difference between the measurements of the first test current and the second test current can range from about one nanosecond to about 100 milliseconds. Also, a time difference between the measurements of the first test current and the third test current can range from about one nanosecond to about 100 milliseconds.

Similar to above, various embodiments of the equation are provided herein. For example, in an exemplary embodiment the equation is $Y=2*abs(i(t))-abs(i(t-x))-abs(i(t+x))$, where $i(t)$ is the second test current, $i(t-x)$ is the first test current, $i(t+x)$ is the third test current, t is a time, and x is an increment of time, and abs represents an absolute function. In one embodiment, the equation is $Z=abs(i(t+x))-abs(i(t))$, where $i(t)$ is the second test current, $i(t+x)$ is the third test current, t is a time, and x is an increment of time, and abs represents an absolute function. These equations can be useful to detect unexpected fast increases or decreases in the current which could indicate that an error with the test has occurred.

Various aspects of a system for determining an analyte concentration or for determining a processing or system error are also provided herein. For example, in one embodiment the system includes an electrochemical cell having at least two electrodes with the cell being sized and configured to receive a sample (e.g., blood). The electrochemical cell can be further configured to determine an initial analyte concentration (e.g., glucose) and also configured to generate a pre-determined voltage between the first and second electrodes for a pre-determined amount of time, and further configured to measure at least one resulting current of the sample during the pre-determined time. The system can also include a processor for receiving a set of data from the electrochemical cell wherein the data can include the initial analyte concentration, a magnitude of at least one (or many) applied voltages, and at least one resulting current. The processor can further be configured to utilize this data to determine a corrected analyte concentration or for determining a system error (e.g., high track resistance, leakage, etc.). In one embodiment, the processor can be utilized to provide a corrected glucose concentration in view of an extreme hematocrit level. In performing this function, the processor utilizes a set of equations to determine a correction term depending on the hematocrit level and the initial glucose concentration. The processor can be configured in various manners to use other equations or parameters depending on the desired calculation and/or the data obtained from the electrochemical cell.

Various aspects of a device for use in determining a corrected analyte concentration are also provided herein. In one such aspect, the device includes a test strip having a sample reaction chamber configured to receive a sample such that the sample is in communication with at least first and second electrodes. The device also includes a reagent layer disposed on at least one electrode wherein the reagent layer is formed of at least one component (e.g., a mediator, enzyme, etc.) configured to react with the sample such that at least two voltages applied to the sample at at least two time intervals results in corresponding currents within the sample which are indicative of an initial analyte concentration and a corrected analyte concentration.

BRIEF DESCRIPTION OF THE DRAWINGS

The present disclosure will be more fully understood from the following detailed description taken in conjunction with the accompanying drawings, in which:

FIG. 2 is a bottom plan view of the test strip of FIG. 1A;

FIG. 3 is a side plan view of the test strip of FIG. 1A;

FIG. 4A is a top plan view of the test strip of FIG. 1A;

FIG. 4B is a partial side view of the distal portion of the test strip consistent with arrows 4B-4B of FIG. 4A;

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

The presently disclosed systems and methods are suitable for use in the determination of a wide variety of analytes in a wide variety of samples, and are particularly suited for use in the determination of analytes in whole blood, plasma, serum, interstitial fluid, or derivatives thereof. In an exemplary embodiment, a glucose test system is provided which is based on a thin-layer cell design with opposing electrodes and triple pulse electrochemical detection which provides a rapid analysis time (e.g., about 5 seconds), requires a small sample (e.g., about 0.4 µL), and provides improved reliability and accuracy of blood glucose measurements. In the reaction cell, glucose in the sample can be oxidized to gluconolactone using glucose dehydrogenase and an electrochemically active mediator can be used to shuttle electrons from the enzyme to a palladium working electrode. A potentiostat can be utilized to apply a triple-pulse potential waveform to the working and counter electrodes, resulting in three current transients used to calculate the glucose concentration. Further, additional information gained from the three current transients may be used to discriminate between sample matrices and correct for variability in blood samples due to hematocrit, temperature variation, or electrochemically active components.

The presently disclosed methods can be used, in principle, with any type of electrochemical cell having spaced apart first and second electrodes and a reagent layer. For example, an electrochemical cell can be in the form of a test strip. In one aspect, the test strip may include two opposing electrodes separated by a thin spacer, for defining a sample-receiving chamber or zone in which a reagent layer is positioned. One skilled in the art will appreciate that other types of test strips, including, for example, test strips with co-planar electrodes as well as configurations with more than two electrodes may also be used with the methods described herein.

Figure 1A:
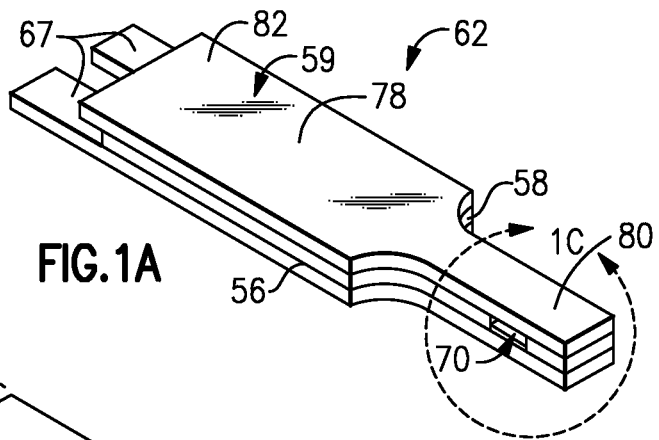
FIG. 1A is a perspective view of a test strip.

FIGS. 1A to 4B show various views of an exemplary test strip 62 suitable for use with the methods and systems described herein. In an exemplary embodiment, a test strip 62 is provided which includes an elongate body 59 extending from a distal end 80 to a proximal end 82, and having lateral edges 56, 58, as illustrated in FIG. 1A. As shown in FIG. 1B, the test strip 62 also includes a first electrode layer 66, a second electrode layer 64, and a spacer 60 sandwiched in between the two electrode layers 64, 66. The first electrode layer 66 can include a first electrode 166, a first connection track 76, and a first contact pad 67, where the first connection track 76 electrically connects the first electrode 166 to the first contact pad 67, as shown in FIGS. 1B and 4B. Note that the first electrode 166 is a portion of the first electrode layer 66 that is immediately underneath the reagent layer 72, as indicated by FIGS. 1B and 4B. Similarly, the second electrode layer 64 can include a second electrode 164, a second connection track 78, and a second contact pad 63, where the second connection track 78 electrically connects the second electrode 164 with the second contact pad 63, as shown in FIGS. 1B, 2, and 4B. Note that the second electrode 64 is a portion of the second electrode layer 164 that is above the reagent layer 72, as indicated by FIG. 4B.

Figure 1B:
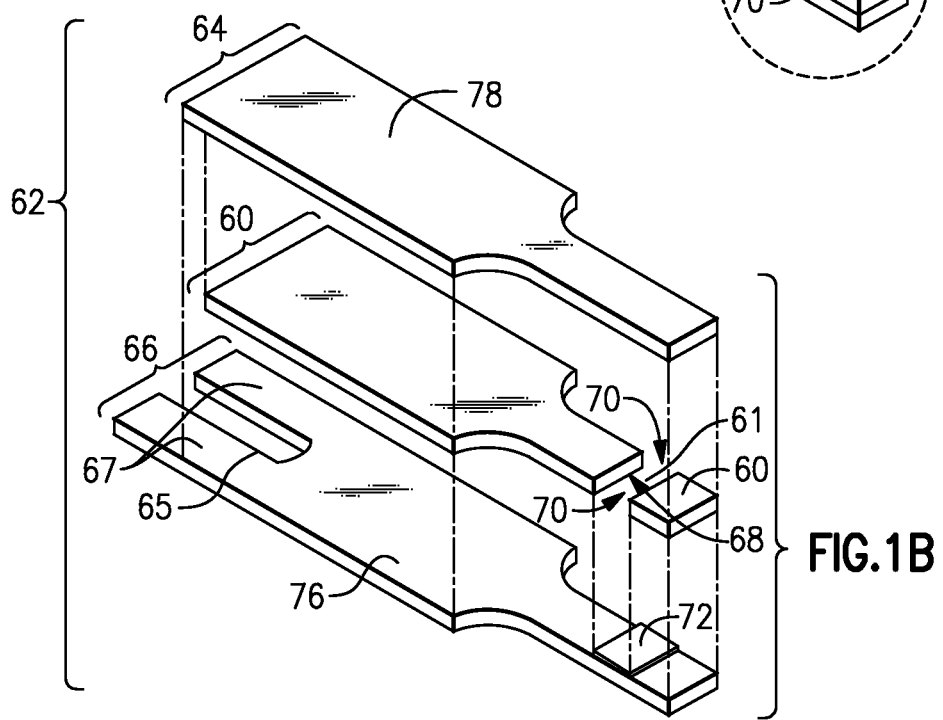
FIG. 1B is an exploded perspective view of the test strip of FIG. 1A.
Figure 1C:
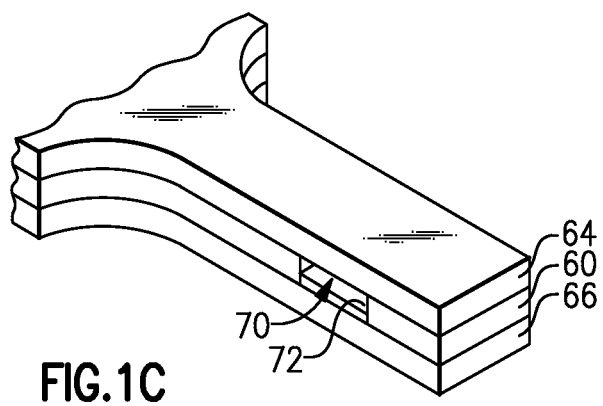
FIG. 1C is a perspective view of a distal portion of the test strip of FIG. 1A.

As shown, a sample-receiving chamber 61 is defined by the first electrode 166, the second electrode 164, and the spacer 60 near the distal end 80 of the test strip 62, as shown in FIG. 1B and FIG. 4B. The first electrode 166 and the second electrode 164 can define the bottom and the top of the sample-receiving chamber 61, respectively, as illustrated in FIG. 4B. A cutout area 68 of the spacer 60 can define the sidewalls of the sample-receiving chamber 61, as illustrated in FIG. 4B. In one aspect, the sample-receiving chamber 61 can include ports 70 that provide a sample inlet and/or a vent, as shown in FIGS. 1A-1C. For example, one of the ports can allow a fluid sample to ingress and the other port can act as a vent.

In an exemplary embodiment, the sample-receiving chamber 61 can have a small volume. For example, the chamber 61 can have a volume in the range of from about 0.1 microliters to about 5 microliters, about 0.2 microliters to about 3 microliters, or, preferably, about 0.3 microliters to about 1 microliter. To provide the small sample volume, the cutout 68 can have an area ranging from about 0.01 cm$^2$ to about 0.2 cm$^2$, about 0.02 cm$^2$ to about 0.15 cm$^2$, or, preferably, about 0.03 cm$^2$ to about 0.08 cm$^2$. In addition, the first electrode 66 and the second electrode 164 can be spaced apart in the range of about 1 micron to about 500 microns, preferably between about 10 microns and about 400 microns, and more preferably between about 40 microns and about 200 microns. The relatively close spacing of the electrodes can also allow redox cycling to occur, where oxidized mediator generated at the first electrode 166, can diffuse to the second electrode 164 to become reduced, and subsequently diffuse back to the first electrode 166 to become oxidized again. Those skilled in the art will appreciate that various such volumes, areas, and/or spacing of electrodes are within the spirit and scope of the present disclosure.

In one embodiment, the first electrode layer 66 and the second electrode layer 64 can be conductive materials formed from materials such as gold, palladium, carbon, silver, platinum, tin oxide, iridium, indium, or combinations thereof (e.g., indium doped tin oxide). In addition, the electrodes can be formed by disposing a conductive material onto an insulating sheet (not shown) by a sputtering, electroless plating, or a screen-printing process. In one exemplary embodiment, the first electrode layer 66 and the second electrode layer 64 can be made from sputtered palladium and sputtered gold, respectively. Suitable materials that can be employed as a spacer 60 include a variety of insulating materials, such as, for example, plastics (e.g., PET, PETG, polyimide, polycarbonate, polystyrene), silicon, ceramics, glass, adhesives, and combinations thereof. In one embodiment, the spacer 60 may be in the form of a double sided adhesive coated on opposing sides of a polyester sheet where the adhesive may be pressure sensitive or heat activated. Those skilled in the art will appreciate that various other materials for the first electrode layer 66, the second electrode layer 64, and/or the spacer 60 are within the spirit and scope of the present disclosure.

Various mechanisms and/or processes can be utilized to dispose a reagent layer 72 within the sample-receiving chamber 61. For example, the reagent layer 72 can be disposed within the sample-receiving chamber 61 using processes such as slot coating, dispensing from the end of a tube, ink jetting, and screen printing. In one embodiment, the reagent layer 72 can include at least a mediator and an enzyme and is deposited onto the first electrode 166. Examples of suitable mediators include ferricyanide, ferrocene, ferrocene derivatives, osmium bipyridyl complexes, and quinone derivatives. Examples of suitable enzymes include glucose oxidase, glucose dehydrogenase (GDH) using a pyrroloquinoline quinone (PQQ) co-factor, GDH using a nicotinamide adenine dinucleotide (NAD) co-factor, and GDH using a flavin adenine dinucleotide (FAD) co-factor [E.C.1.1.99.10]. The reagent layer 72 can be prepared from a formulation that contains 33 mM potassium citraconate, pH 6.8, 0.033% Pluronic P103, 0.017% Pluronic F87, 0.85 mM CaCl$_2$, 30 mM sucrose, 286 µM PQQ, 15 mg/mL GDH, and 0.6 M ferricyanide. Pluronics are block copolymers based on ethylene oxide and propylene oxide, which can function as antifoaming agents and/or wetting agents.

The formulation can be applied at some desired rate (e.g., about 570 µL/min) using a 13 gauge needle poised about 150 µm above a palladium web moving at about 10 m/min. Before coating the palladium web with the enzyme formulation, the web can be coated with 2-mercaptoethane sulfonic acid (MESA). A spacer having a desired thickness (e.g., about 95 µm) with a channel cut therein having some desired width (e.g., a width of about 1.2 mm) can be laminated to the reagent layer and the palladium web at some desired temperature (e.g., about 70° C.). A MESA-coated gold web can be laminated to the other side of the spacer. The spacer can be made from a polymer substrate such as polyester coated on both sides with a thermoplastic adhesive such as Vitel, which is a linear saturated copolyester resin having a relatively high molecular weight. Release liners can optionally be laminated on top of the adhesive layer on each side of the spacer to protect the adhesive until lamination. The resulting laminate can be cut such that the fill path of the sample-receiving chamber is about 3.5 mm long, thus giving a total volume of about 0.4 µL.

In one embodiment, the reagent layer 72 may have an area larger than the area of the first electrode 166. A portion of the spacer 60 may overlap and touch the reagent layer 72. The spacer 60 may be configured to form a liquid impermeable seal to the first electrode 166 even though a portion of the reagent layer 72 is between the spacer 60 and the first electrode 166. The spacer 60 may intermingle or partially dissolve a portion of the reagent layer 72 to form a liquid impermeable bond to the first electrode 166 sufficient to define the electrode area for at least the total test time. Under certain circumstances where the reagent layer 72 is not sufficiently dry or there is contamination such as dust particles present, the spacer 60 may not be able to form a liquid impermeable seal and, as a result, the liquid may seep between the spacer 60 and the first electrode 166. Such a leakage event may cause an inaccurate glucose measurement to occur.

Either the first electrode 166 or the second electrode 164 can perform the function of a working electrode depending on the magnitude and/or polarity of the applied test voltage. The working electrode may measure a limiting test current that is proportional to the reduced mediator concentration. For example, if the current limiting species is a reduced mediator (e.g., ferrocyanide), then it can be oxidized at the first electrode 166 as long as the test voltage is sufficiently more positive than the redox mediator potential with respect to the second electrode 164. In such a situation, the first electrode 166 performs the function of the working electrode and the second electrode 164 performs the function of a counter/reference electrode. One skilled in the art may refer to a counter/reference electrode simply as a reference electrode or a counter electrode. A limiting oxidation occurs when all reduced mediator has been depleted at the working electrode surface such that the measured oxidation current is proportional to the flux of reduced mediator diffusing to the working electrode surface. It should be noted that unless otherwise stated for test strip 62, all potentials applied by the test meter 100 will hereinafter be stated with respect to the second electrode 164.

Similarly, if the test voltage is sufficiently more negative than the redox mediator potential, then the reduced mediator can be oxidized at the second electrode 164 as a limiting current. In such a situation, the second electrode 164 performs the function of the working electrode and the first electrode 166 performs the function of the counter/reference electrode.

Initially, performing an analysis can include introducing a quantity of a fluid sample into a sample-receiving chamber 61 via a port 70. In one aspect, the port 70 and/or the sample-receiving chamber 61 can be configured such that capillary action causes the fluid sample to fill the sample-receiving chamber 61. The first electrode 166 and/or second electrode 164 may be coated with a hydrophilic reagent to promote the capillarity of the sample-receiving chamber 61. For example, thiol derivatized reagents having a hydrophilic moiety such as 2-mercaptoethane sulfonic acid may be coated onto the first electrode and/or the second electrode.

Figure 5:
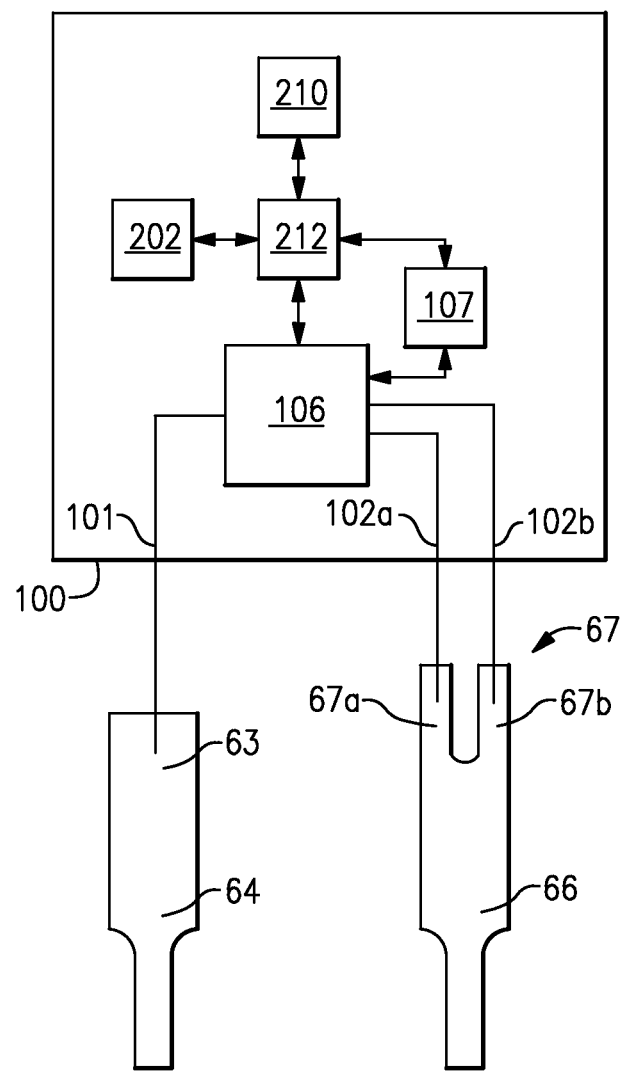
FIG. 5 is a simplified schematic showing a test meter electrically interfacing with the test strip contact pads.

FIG. 5 provides a simplified schematic showing a test meter 100 interfacing with a first contact pad 67a, 67b and a second contact pad 63. The second contact pad 63 can be used to establish an electrical connection to the test meter through a U-shaped notch 65, as illustrated in FIG. 2. In one embodiment, the test meter 100 may include a second electrode connector 101, and first electrode connectors 102a, 102b, a test voltage unit 106, a current measurement unit 107, a processor 212, a memory unit 210, and a visual display 202, as shown in FIG. 5. The first contact pad 67 can include two prongs 67a, 67b. In one embodiment, the first electrode connectors 102a, 102b separately connect to the prongs 67a, 67b, respectively. The second electrode connector 101 can connect to the second contact pad 63. The test meter 100 can measure the resistance or electrical continuity between the prongs 67a, 67b to determine whether the test strip 62 is electrically connected to the test meter 100. One skilled in the art will appreciate that the test meter 100 can use a variety of sensors and circuits to determine when the test strip 62 is properly positioned with respect to the test meter 100.

In one embodiment, the test meter 100 can apply a test voltage and/or a current between the first contact pad 67 and the second contact pad 63. Once the test meter 100 recognizes that the strip 62 has been inserted, the test meter 100 turns on and initiates a fluid detection mode. In one embodiment, the fluid detection mode causes the test meter 100 to attempt to apply a voltage such that a constant current of about 0.5 microampere would flow between the first electrode 166 and the second electrode 164. Because the test strip 62 is initially dry, the test meter 100 measures a relatively large voltage, which can be limited by the maximum voltage that the test meter is capable of supplying. When the fluid sample bridges the gap between the first electrode 166 and the second electrode 164 during the dosing process, the test meter 100 will measure a decrease in applied voltage and when it is below a predetermined threshold will cause the test meter 100 to automatically initiate the glucose test.

Figure 6:
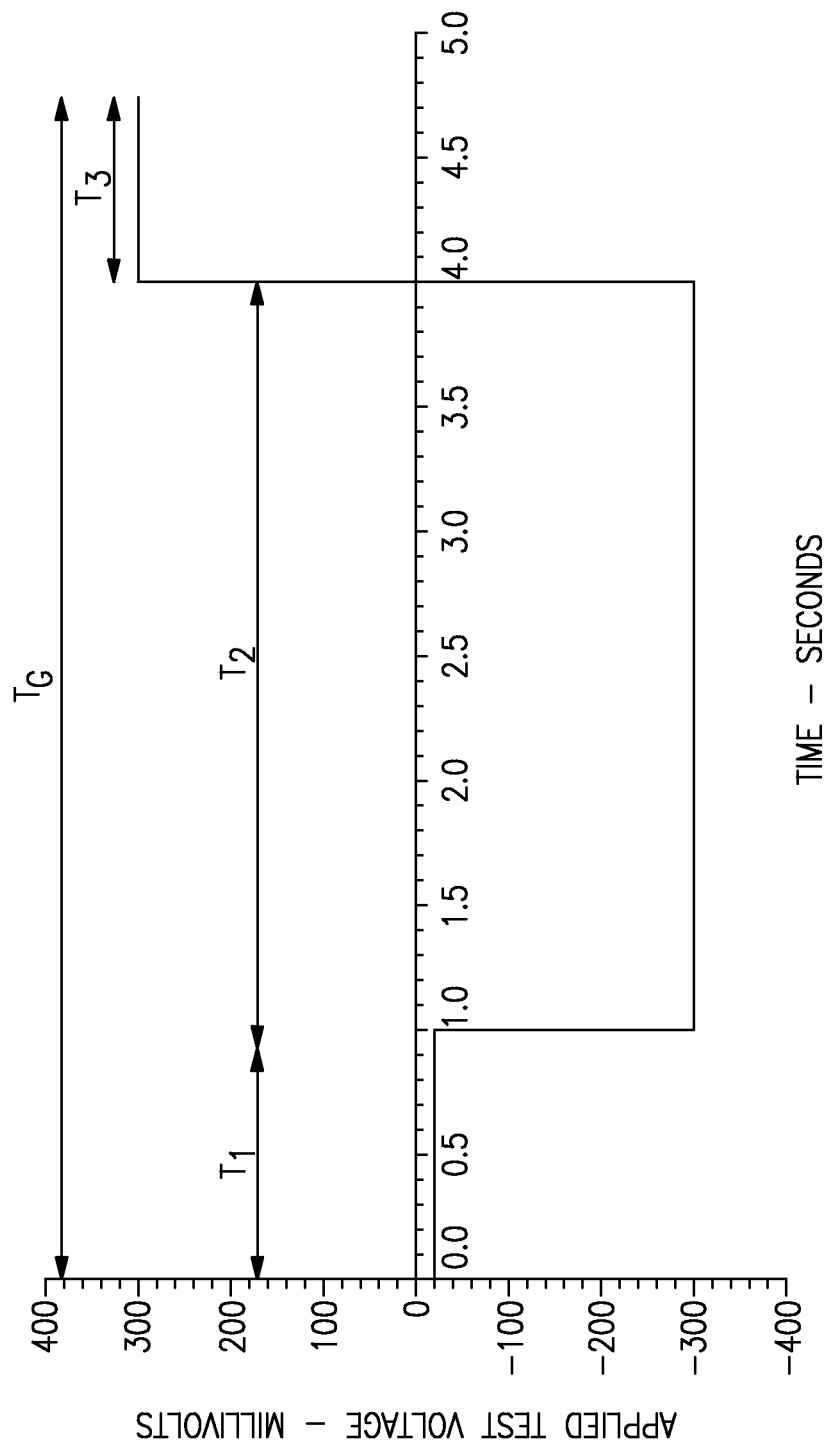
FIG. 6 shows a test voltage waveform in which the test meter applies a plurality of test voltages for prescribed time intervals.

In one embodiment, the test meter 100 can perform a glucose test by applying a plurality of test voltages for prescribed intervals, as shown in FIG. 6. The plurality of test voltages may include a first test voltage $V_1$ for a first time interval $T_1$, a second test voltage $V_2$ for a second time interval $T_2$, and a third test voltage $V_3$ for a third time interval $T_3$. A glucose test time interval $T_G$ represents an amount of time to perform the glucose test (but not necessarily all the calculations associated with the glucose test). The glucose test time interval $T_G$ can range from about 1 second to about 15 seconds or longer and more preferably from about 1 second to about 5 seconds. The plurality of test current values measured during the first, second, and third time intervals may be performed at a frequency ranging from about 1 measurement per nanosecond to about one measurement per 100 milliseconds. While an embodiment using three test voltages in a serial manner is described, one skilled in the art will appreciate that the glucose test can include different numbers of open-circuit and test voltages. For example, as an alternative embodiment, the glucose test could include an open-circuit for a first time interval, a second test voltage for a second time interval, and a third test voltage for a third time interval. One skilled in the art will appreciate that names "first," "second," and "third" are chosen for convenience and do not necessarily reflect the order in which the test voltages are applied. For instance, an embodiment can have a potential waveform where the third test voltage can be applied before the application of the first and second test voltage.

Once the glucose assay has been initiated, the test meter 100 may apply a first test voltage $V_1$ (e.g., about −20 mV as shown in FIG. 6) for a first time interval $T_1$ (e.g., about 1 second as shown in FIG. 6). The first time interval $T_1$ can range from about 0.1 seconds to about 3 seconds and preferably range from about 0.2 seconds to about 2 seconds, and most preferably range from about 0.3 seconds to about 1 seconds.

Figure 7:
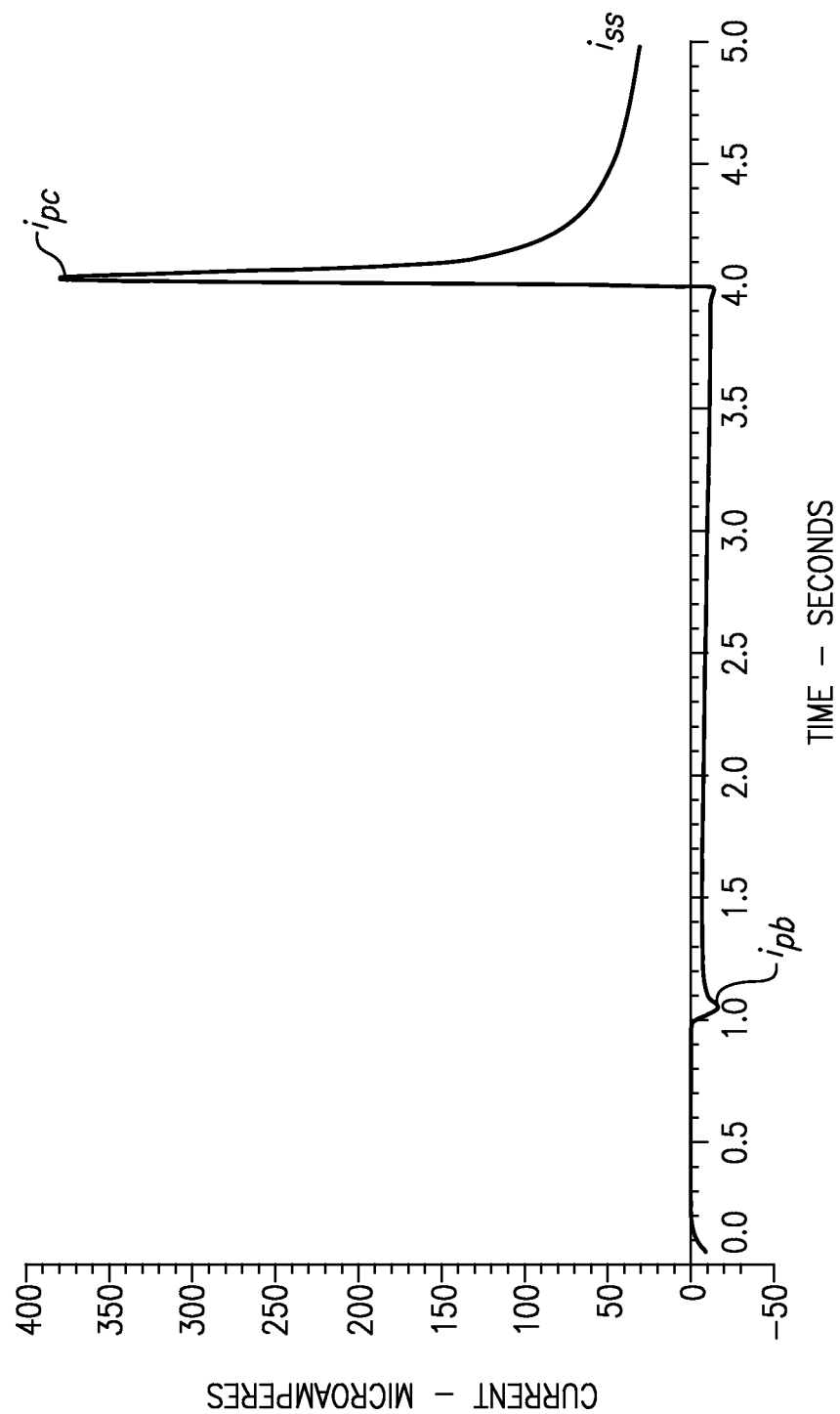
FIG. 7 shows a test current transient generated with the test voltage waveform of FIG. 6.

The first time interval $T_1$ may be sufficiently long so that the sample-receiving chamber 61 can fully fill with sample and also so that the reagent layer 72 can at least partially dissolve or solvate. In one aspect, the first test voltage $V_1$ may be a relatively low value so that a relatively small amount of a reduction or oxidation current is measured. FIG. 7 shows that a relatively small amount of current is observed during the first time interval $T_1$ compared to the second and third time intervals $T_2$ and $T_3$. For example, when using ferricyanide and/or ferrocyanide as the mediator, the first test voltage $V_1$ can range from about −100 mV to about −1 mV, preferably range from about −50 mV to about −5 mV, and most preferably range from about −30 mV to about −10 mV.

After applying the first test voltage $V_1$, the test meter 100 applies a second test voltage $V_2$ between the first electrode 166 and the second electrode 164 (e.g., about −0.3 Volts as shown in FIG. 6), for a second time interval $T_2$ (e.g., about 3 seconds as shown in FIG. 6). The second test voltage $V_2$ may be a value sufficiently negative of the mediator redox potential so that a limiting oxidation current is measured at the second electrode 164. For example, when using ferricyanide and/or ferrocyanide as the mediator, the second test voltage $V_2$ can range from about −600 mV to about zero mV, preferably range from about −600 mV to about −100 mV, and more preferably be about −300 mV.

The second time interval $T_2$ should be sufficiently long so that the rate of generation of reduced mediator (e.g., ferrocyanide) can be monitored based on the magnitude of a limiting oxidation current. Reduced mediator is generated by enzymatic reactions with the reagent layer 72. During the second time interval $T_2$, a limiting amount of reduced mediator is oxidized at the second electrode 164 and a non-limiting amount of oxidized mediator is reduced at the first electrode 166 to form a concentration gradient between the first electrode 66 and the second electrode 164.

In an exemplary embodiment, the second time interval $T_2$ should also be sufficiently long so that a sufficient amount of ferricyanide can be generated at the second electrode 164. A sufficient amount of ferricyanide is required at the second electrode 164 so that a limiting current can be measured for oxidizing ferrocyanide at the first electrode 166 during the third test voltage $V_3$. The second time interval $T_2$ may be less than about 60 seconds, preferably range from about 1 second to about 10 seconds, and more preferably range from about 2 seconds to about 5 seconds.

FIG. 7 shows a relatively small peak $i_{pb}$ at the beginning of the second time interval $T_2$ followed by a gradual increase of an absolute value of an oxidation current during the second time interval $T_2$. The small peak $i_{pb}$ occurs due to an initial depletion of reduced mediator at about 1 second. The gradual increase in oxidation current after the small peak $i_{pb}$ is caused by the generation of ferrocyanide by reagent layer 72, which then diffuses to second electrode 164.

After applying the second test voltage $V_2$, the test meter 100 applies a third test voltage $V_3$ between the first electrode 166 and the second electrode 164 (e.g., about +0.3 Volts in FIG. 6) for a third time interval $T_3$ (e.g., 1 second in FIG. 6). The third test voltage $V_3$ may be a value sufficiently positive of the mediator redox potential so that a limiting oxidation current is measured at the first electrode 166. For example, when using ferricyanide and/or ferrocyanide as the mediator, the third test voltage $V_3$ can range from about 0 mV to about 600 mV, preferably range from about 100 mV to about 600 mV, and more preferably be about 300 mV.

The third time interval $T_3$ may be sufficiently long to monitor the diffusion of reduced mediator (e.g., ferrocyanide) near the first electrode 166 based on the magnitude of the oxidation current. During the third time interval $T_3$, a limiting amount of reduced mediator is oxidized at first electrode 166 and a non-limiting amount of oxidized mediator is reduced at the second electrode 164. The third time interval $T_3$ can range from about 0.1 seconds to about 5 seconds and preferably range from about 0.3 seconds to about 3 seconds, and more preferably range from about 0.5 seconds to about 2 seconds.

FIG. 7 shows a relatively large peak $i_{pc}$ at the beginning of the third time interval $T_3$ followed by a decrease to a steady-state current $i_{ss}$ value. In one embodiment, the second test voltage $V_2$ can have a first polarity and the third test voltage $V_3$ may have a second polarity that is opposite to the first polarity. In another embodiment, the second test voltage $V_2$ can be sufficiently negative of the mediator redox potential and the third test voltage $V_3$ can be sufficiently positive of the mediator redox potential. The third test voltage $V_3$ may be applied immediately after the second test voltage $V_2$. However, one skilled in the art will appreciate that the magnitude and polarity of the second and third test voltages can be chosen depending on the manner in which analyte concentration is determined.

Assuming that a test strip has an opposing face or facing arrangement as shown in FIGS. 1A-4B, and that a potential waveform is applied to the test strip as shown in FIG. 6, an initial glucose concentration $G_1$ can be calculated using a glucose algorithm as shown in Equation 1.

$$G_1 = \left(\frac{i_2^p}{i_3}\right)^p \times (a \times i_1 - z) \quad \text{Eq. 1}$$

In Equation 1, $i_1$ is a first test current value, $i_2$ is a second test current value, and $i_3$ is a third test current value, and the terms p, z, and a are empirically derived calibration constants. All test current values (i.e., $i_1$, $i_2$, and $i_3$) in Equation 1 use the absolute value of the current. The first test current value $i_1$ and the second test current value $i_2$ can each be defined by an average or summation of one or more predetermined test current values that occur during the third time interval $T_3$. The third test current value $i_3$ can be defined by an average or summation of one or more predetermined test current values that occur during the second time interval $T_2$. One skilled in the art will appreciate that names "first," "second," and "third" are chosen for convenience and do not necessarily reflect the order in which the current values are calculated.

Equation 1 can be modified to provide an even more accurate glucose concentration. Instead of using a simple average or summation of test current values, the term $i_1$ can be defined to include peak current values $i_{pb}$ and $i_{pc}$ and the steady-state current $i_{ss}$, as shown in Equation 2.

$$i_1 = i_2 \left\{ \frac{i_{pc} - 2i_{pb} + i_{ss}}{i_{pc} + i_{ss}} \right\} \quad \text{Eq. 2}$$

A calculation of the steady-state current $i_{ss}$ can be based on a mathematical model, an extrapolation, an average at a predetermined time interval, or a combination thereof. One example of a method for calculating $i_{ss}$ can be found in U.S. Pat. No. 6,413,410 and U.S. Pat. No. 5,942,102, the entirety of these patents being incorporated herein by reference.

Equation 2 can be combined with Equation 1 to give Equation 3 for determining a more accurate glucose concentration that can compensate for the presence of endogenous and/or exogenous interferents in a blood sample.

$$G_1 = \left(\frac{i_2}{i_3}\right)^p \times \left(a \times i_2 \times \left\{\frac{i_{pc} - 2i_{pb} + i_{ss}}{i_{pc} + i_{ss}}\right\} - z\right) \quad \text{Eq. 3}$$

In addition to endogenous interferents, extreme hematocrit levels under certain circumstances can affect the accuracy of a glucose measurement. Thus, Equation 3 can be further modified to provide a corrected glucose concentration $G_2$ that is accurate even if the sample has an extreme hematocrit level (e.g., about 10% or about 70%).

Additionally, various embodiments of a method and system configured to account for and/or identify various system, user, and/or device inefficiencies and/or errors are provided herein. For example, in one embodiment, the system can accurately determine a glucose concentration of a sample having an extreme hematocrit level. Additionally, the system can be configured to identify a test utilizing a partial fill or double-fill of a sample chamber. Also, the system can be configured to identify those situations where the sample may be leaking from the sample chamber thereby compromising the integrity of the testing and/or those situations where some portion of system (e.g., the test strip) is damaged. These various embodiments are described below.

Figure 8:
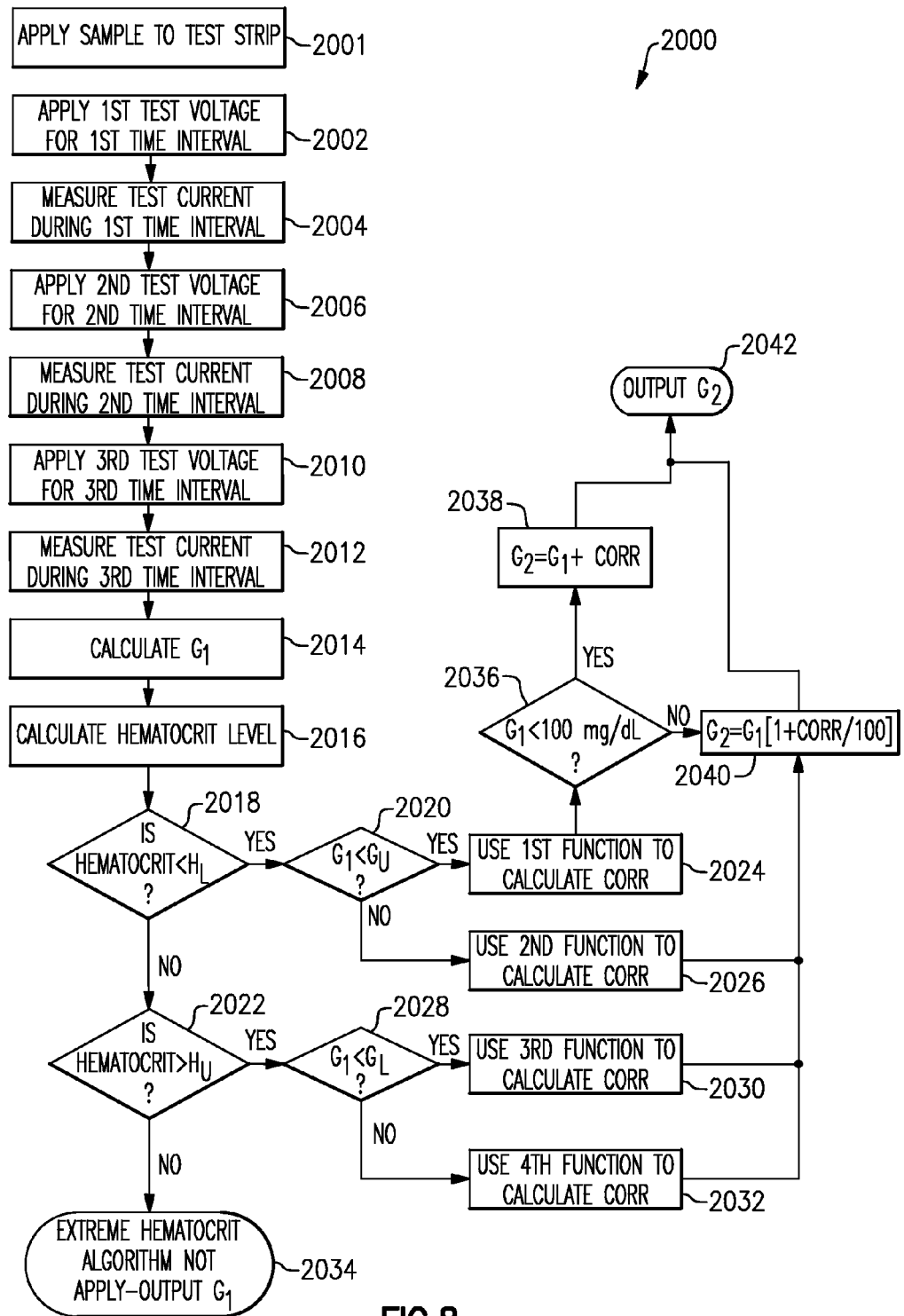
FIG. 8 is a flow diagram depicting an exemplary embodiment of a method of calculating an analyte concentration for samples having an extreme hematocrit level.

Analyte Detection at Extreme Hematocrit Levels:

Methods and systems of accurately measuring glucose concentrations in extreme hematocrit samples are provided herein. For example, FIG. 8 is a flow diagram depicting a method 2000 for calculating an accurate glucose concentration that accounts for blood samples having an extreme hematocrit level. A user can initiate a test by applying a sample to the test strip, as shown in step 2001. A first test voltage $V_1$ can be applied for a first time interval $T_1$, as shown in step 2002. The resulting test current is then measured for the first time interval $T_1$, as shown in step 2004. After the first time interval $T_1$, the second test voltage $V_2$ is applied for a second time interval $T_2$, as shown in step 2006. The resulting test current is then measured for the second time interval $T_2$, as shown in step 2008. After the second time interval $T_2$, the third test voltage $V_3$ is applied for a third time interval $T_3$, as shown in step 2010. The resulting test current is then measured for the third time interval $T_3$, as shown in step 2012.

Now that test current values have been collected by a test meter, an initial glucose concentration $G_1$ can be calculated, as shown in step 2014. The initial glucose concentration $G_1$ can be calculated using Equation 1 or Equation 3. Next, a hematocrit level H can be calculated, as shown in step 2016.

The hematocrit level may be estimated using test current values acquired during the glucose test time interval $T_G$. Alternatively, the hematocrit level H may be estimated using test current values acquired during the second time interval $T_2$ and the third time interval $T_3$. In one embodiment, the hematocrit level H can be estimated using a hematocrit equation based upon the initial glucose concentration $G_1$ and the second test current value $i_2$. An exemplary hematocrit equation is shown in Equation 4.

$$H=K_5 \ln(|i_2|)+K_6 \ln(G_1)+K_7 \quad \text{Eq.4}$$

Figure 9:
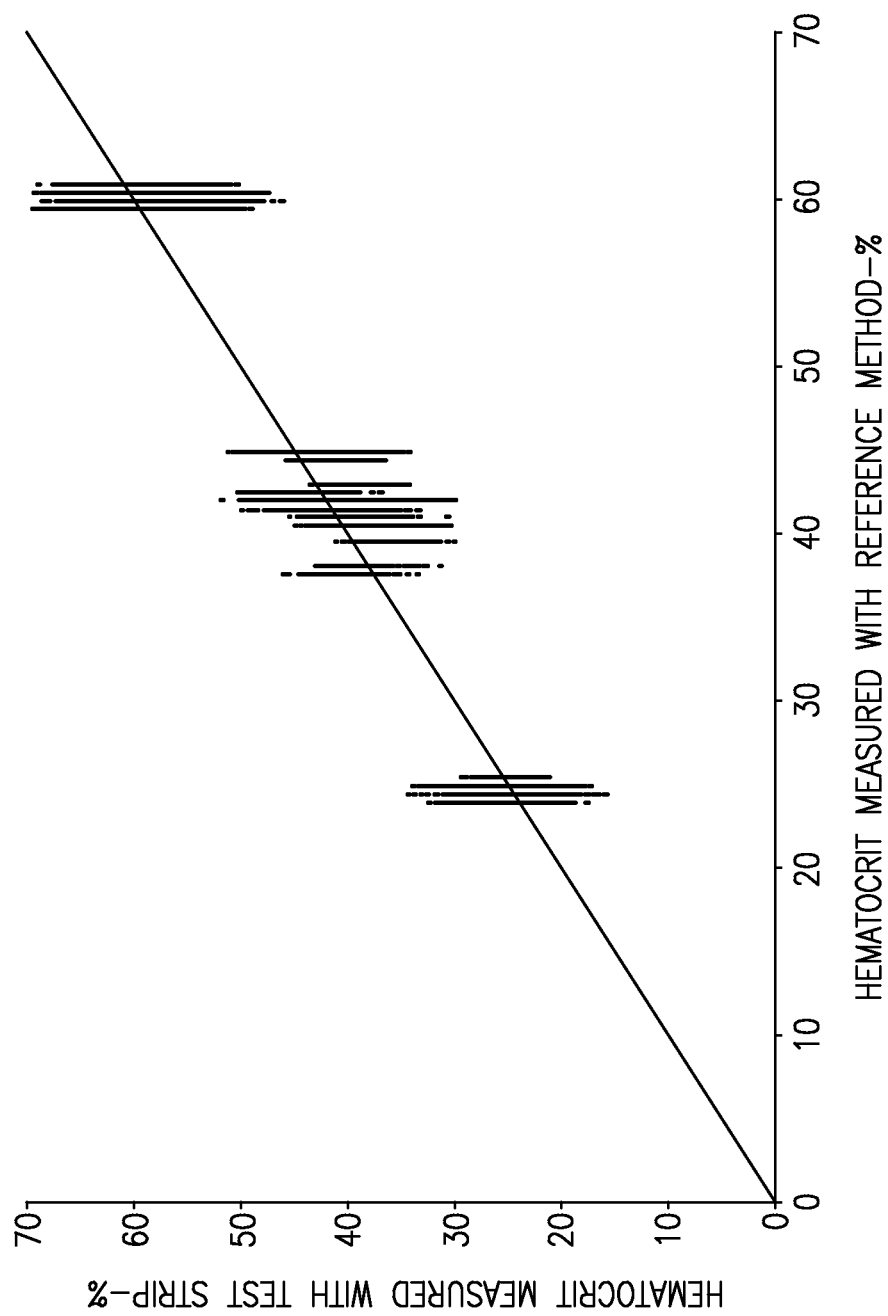
FIG. 9 is a chart showing a correlation between measured hematocrit levels using a reference method and measured hematocrit levels using the test strip of FIG. 1.

The term H is the hematocrit level, $i_2$ is at least one current value during the second time interval, $K_5$ is a fifth constant, $K_6$ is a sixth constant, and $K_7$ is a seventh constant. In one embodiment, $K_5$, $K_6$, and $K_7$ may be $-76$, 56, and, 250, respectively. FIG. 9 shows that the estimated hematocrit levels using Equation 4 has an approximately linear correlation with actual hematocrit levels measured with a reference method.

Once the hematocrit level H has been calculated in step 2016, it is compared to a lower predetermined hematocrit level $H_L$, as shown in step 2018. The lower predetermined hematocrit level $H_L$ may be about 30%. If the hematocrit level H is less than the lower predetermined hematocrit level $H_L$, then the initial glucose concentration $G_1$ is compared to an upper predetermined glucose concentration $G_U$, as shown in step 2020. The upper predetermined glucose concentration $G_U$ may be about 300 mg/dL. If the hematocrit level H is not less than the lower predetermined hematocrit level $H_L$, then the hematocrit level H is compared to an upper predetermined hematocrit level $H_U$, as shown in step 2022. The upper predetermined hematocrit level $H_U$ may be about 50%. If the hematocrit level H is greater than $H_U$, then the initial glucose concentration $G_1$ is compared to a lower predetermined glucose concentration $G_L$, as shown in step 2028. The lower predetermined glucose concentration $G_L$ may be about 100 mg/dL. Steps 2018 and 2022 indicate that method 2000 will output the initial glucose concentration $G_1$, as shown in step 2034, if the hematocrit level H is not less than $H_L$ and not greater than $H_U$.

A first function can be used to calculate a correction value Corr, as shown in step 2024, if H is less than $H_L$ and if the initial glucose concentration $G_1$ is less than the upper predetermined glucose concentration $G_U$. The first function may be in the form of Equation 5.

$$\text{Corr}=K_1(H_L-H)G_1 \quad \text{Eq.5}$$

The term $K_1$ is a first constant and $H_L$ is the lower predetermined hematocrit level. In one embodiment, $K_1$ and $H_L$ may be $-0.004$ and about 30%, respectively.

However, if H is less than $H_L$ and if the initial glucose concentration $G_1$ is not less than the upper predetermined glucose concentration $G_U$, then the second function can be used to calculate the correction value Corr, as shown in step 2026. The second function may be in the form of Equation 6.

$$\text{Corr}=K_2(H_L-(G_{max}-G_1)) \quad \text{Eq.6}$$

The term $K_2$ is a second constant and $G_{max}$ is a predetermined maximum glucose concentration. In one embodiment, $K_2$ and $G_{max}$ may be $-0.004$ and about 600 mg/dL, respectively. The correction value Corr for Equations 5 and 6 may be restricted to a range of about $-5$ to about zero. Thus, if Corr is less than $-5$, then Corr is set to $-5$ and if Corr is greater than zero then Corr is set to zero.

A third function can be used to calculate a correction value Corr, as shown in step 2030, if H is greater than $H_U$ and if the initial glucose concentration $G_1$ is less than a lower predetermined glucose concentration $G_L$. The third function may be in the form of Equation 7.

$$\text{Corr}=0 \quad \text{Eq.7}$$

However, if H is greater than $H_U$ and if the initial glucose concentration $G_1$ is not less than the lower predetermined glucose concentration $G_L$, then the fourth function can be used to calculate the correction value Corr, as shown in a step 2032. The fourth function may be in the form of Equation 8.

$$\text{Corr}=K_4(H-H_U)(G_1-G_L) \quad \text{Eq.8}$$

The term $K_4$ is a fourth constant, which may be about 0.011. The correction value Corr for Equation 8 may be restricted to a range of about zero to about six. Thus, if Corr is less than zero, then Corr is set to zero and if Corr is greater than six then Corr is set to six.

After calculating Corr with the first function in step 2024, the first glucose concentration is compared to 100 mg/dL in step 2036. If the first glucose concentration is less than 100 mg/dL, then the second glucose concentration $G_2$ is calculated using a first correction equation, as shown in step 2038. Note that the 100 mg/dL represents a glucose threshold and should not be construed as a limiting number. In one embodiment, the glucose threshold may range from about 70 mg/dL to about 100 mg/dL. The first correction equation may be in the form of Equation 9.

$$G_2=G_1+\text{Corr} \quad \text{Eq.9}$$

If the initial glucose concentration $G_1$ is not less than 100 mg/dL based on step 2036, then the corrected glucose concentration $G_2$ is calculated using a second correction equation, as shown in step 2040. The second correction equation may be in the form of Equation 10.

$$G_2 = G_1\left(1 + \frac{\text{Corr}}{100}\right) \qquad \text{Eq. 10}$$

After the corrected glucose concentration $G_2$ is calculated in either step 2038 or step 2040, it is outputted as a glucose reading in step 2042.

After calculating Corr in step 2026, step 2030, or step 2032, the corrected glucose concentration $G_2$ can be calculated using Equation 10, as shown in step 2040. When Corr equals zero (as for the third function), the corrected glucose concentration $G_2$ equals the initial glucose concentration $G_1$, which can then be outputted as a glucose reading in step 2042.

Figure 10:
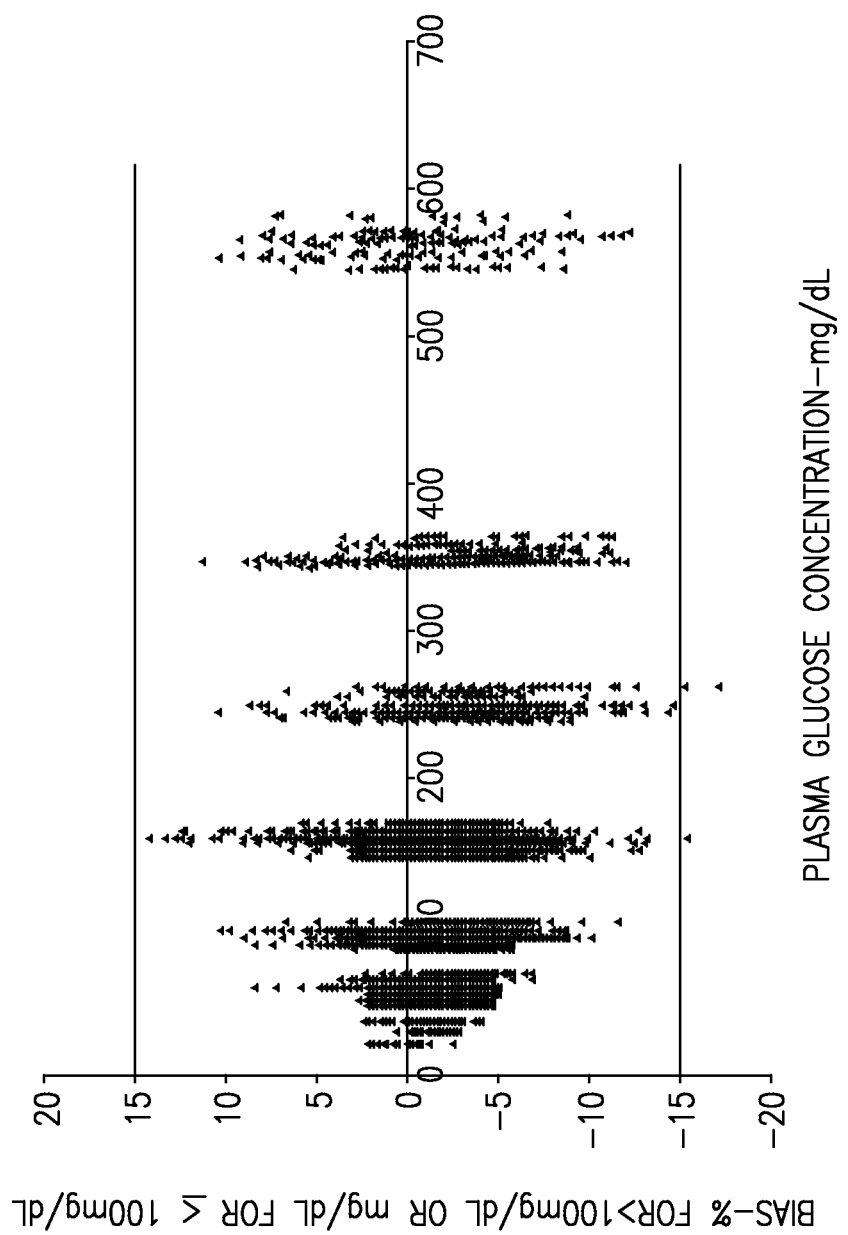
FIG. 10 is a bias plot showing a plurality of test strips that were tested with blood samples having a wide range of hematocrit levels.

The method 2000 for calculating accurate glucose concentrations in blood samples having extreme hematocrit levels was verified using blood from several donors. FIG. 10 shows a bias plot for a plurality of test strips that were tested with blood samples having a wide range of hematocrit levels and glucose concentrations. More specifically, FIG. 10 shows the effect of whole blood samples having a wide range of hematocrit on the accuracy and precision of the new test system. As shown, the bias of the sensor response with respect to the YSI 2700 instrument (Yellow Springs Instruments, Yellow Springs, Ohio) is plotted against the plasma glucose concentration. The data were obtained with 3 batches of sensors and 4 blood donors. The hematocrit was adjusted to 20% (squares), 37-45% (circles) or 60% (triangles) prior to spiking the samples with glucose. These data suggest that the thin layer cell and triple-pulse approach for electrochemical measurement offers the opportunity for improved analytical performance with blood glucose test systems. Thus, the use of the correction value Corr, which depends on the hematocrit level H and the initial glucose concentration $G_1$, allows for the determination of a more accurate corrected glucose concentration $G_2$ even if the blood sample has an extreme hematocrit level.

Figure 11:
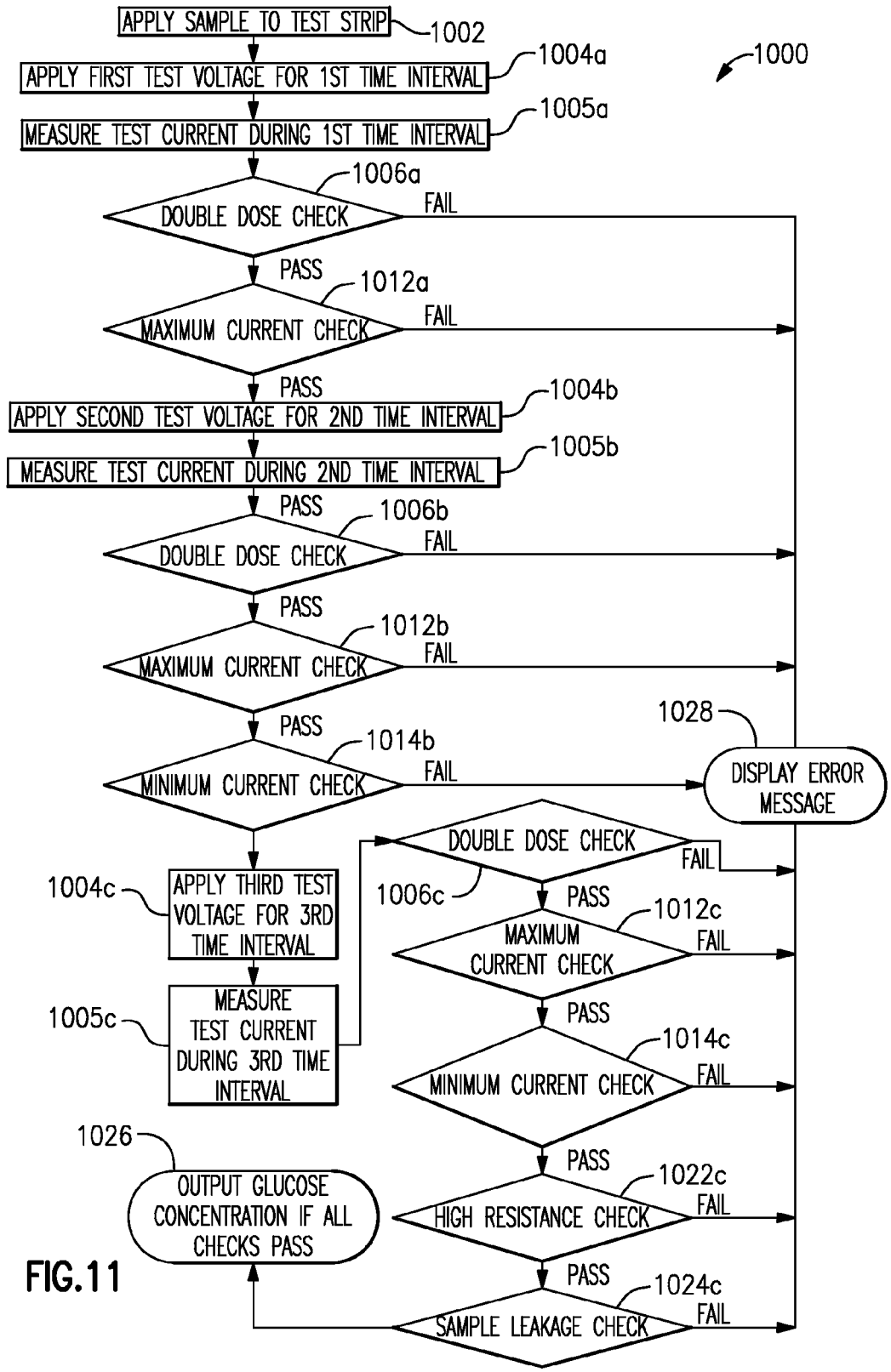
FIG. 11 is a flow diagram depicting an embodiment of a method of identifying system errors.

Identifying System Errors:

Various embodiments of a method for identifying system errors, which may include user errors when performing a test, test meter errors, and defective test strips, are also provided. For example, FIG. 11 is a flow diagram depicting an exemplary embodiment of a method 1000 of identifying system errors in performing an analyte measurement. As shown, a user can initiate a test by applying a sample to a test strip, as shown in step 1002. After the sample has been dosed, the test meter applies a first test voltage $V_1$ for a first time interval $T_1$, as shown in step 1004a. A resulting test current is then measured for the first time interval $T_1$, as shown in step 1005a. During the first time interval $T_1$, the test meter performs a double dose check 1006a, and a maximum current check 1012a. If either the double dose check 1006a or maximum current check 1012a fails, then the test meter will display an error message, as shown in step 1028. If the double dose check 1006a and maximum current check 1012a both pass, then the test meter can apply a second test voltage $V_2$ for a second time interval $T_2$, as shown in step 1004b.

A resulting test current is measured for the second time interval $T_2$, as shown in step 1005b. During the application of the second test voltage $V_2$, the test meter performs a double dose check 1006b, a maximum current check 1012b, and a minimum current check 1014b. If one of the checks 1006b, 1012b, or 1014b fail, then the test meter will display an error message, as shown in step 1028. If all of the checks 1006b, 1012b, and 1014b pass, then the test meter will apply a third test voltage $V_3$, as shown in step 1004c.

A resulting test current is measured for the third time interval $T_3$, as shown in step 1005c. During the application of the third test voltage $V_3$, the test meter performs a double dose check 1006c, maximum current check 1012c, a minimum current check 1014c, a high resistance check 1022c, and a sample leakage check 1024c. If all of the checks 1006c, 1012c, 1014c, 1022c, and 1024c pass, then the test meter will display a glucose concentration, as shown in step 1026. If one of the checks 1006c, 1012c, 1014c, 1022c, and 1024c fails, then the test meter will display an error message, as shown in step 1028.

Double-Dosing Events

Figure 12:
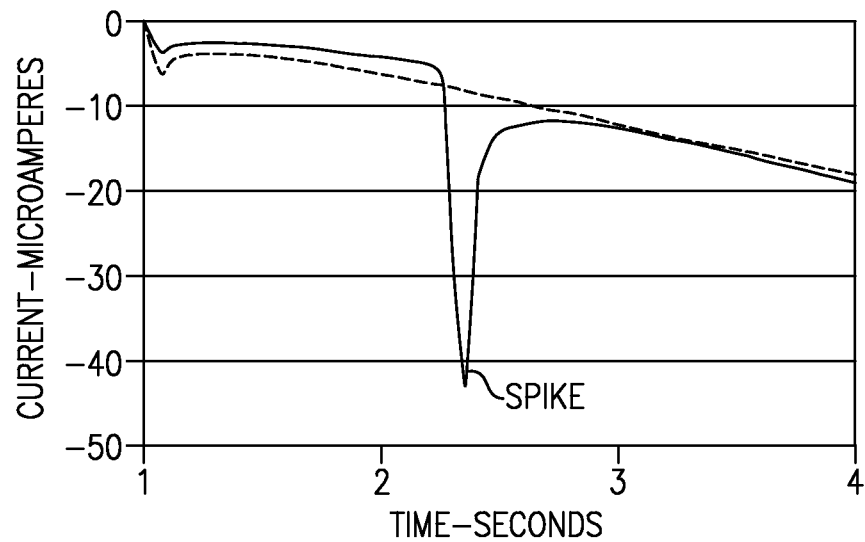
FIG. 12 shows a test current transient of the second test time interval when a user performs a double dose (solid line) and does not perform a double dose (dotted line)

A double dose occurs when a user applies an insufficient volume of blood to a sample-receiving chamber and then applies a subsequent bolus of blood to further fill the sample-receiving chamber. An insufficient volume of blood expressed on a user's fingertip or a shaky finger can cause the occurrence of a double-dosing event. The currently disclosed system and method can be configured to identify such double-fill events. For example, FIG. 12 shows a test current transient where a double-dosing event occurs during the second test time interval $T_2$ thereby causing a spike to be observed (see solid line). When there is no double-dosing event, the test current transient does not have a peak (see dotted line of FIG. 12).

A double-dosing event can cause a glucose test to have an inaccurate reading. Thus, it is usually desirable to identify a double-dosing event and then have the meter output an error message instead of outputting a potentially inaccurate reading. A double-dosing event initially causes the measured test current to be low in magnitude because the electrode area is effectively decreased when only a portion is wetted with sample. Once the user applies the second dose, a current spike will occur because of a sudden increase in the effective electrode area and also because turbulence causes more reduced mediator to be transported close to the working electrode. In addition, less ferrocyanide will be generated because a portion of the reagent layer is not wetted by the sample for the entire test time. Thus, an inaccurate glucose reading can result if a test current value used in the glucose algorithm is depressed or elevated as a result of the double-dosing.

A method of identifying a double-dosing event (1006a, 1006b, or 1006c) may include measuring a second test current and a third test current where the second test current occurs before the third test current. An equation may be used to identify double-dosing events based on a difference between the absolute value of the third test current and the absolute value of the second test current. If the difference is greater than a predetermined threshold, the test meter can output an error message indicative of a double-dosing event. The method of identifying the double-dosing event may be performed multiple times in serial manner as the test current values are collected by the test meter. The equation can be in the form of Equation 11 for calculating a difference value Z for determining whether a double-dosing event had occurred.

$$Z = abs(i(t+x)) - abs(i(t)) \qquad \text{Eq.11}$$

The terms $i(t)$ is a second test current, $i(t+x)$ is a third test current, t is a time for the second test current, and x is an increment of time in between current measurements. If the value Z is greater than a predetermined threshold of about 3 microamperes, then the test meter may output an error message due to a double-dosing event. The predetermined thresholds disclosed herein are illustrative for use with test strip 100 and with the test voltage waveform of FIG. 6 where the working electrode and the reference electrode both have an area of about 0.042 cm$^2$ and a distance between the two electrodes ranging from about 90 microns to about 100 microns. It should be obvious to one skilled in the art that such predetermined thresholds may change based on the test strip design, the test voltage waveform, and other factors.

In another embodiment for identifying a double-dosing event (e.g., 1006a, 1006b, or 1006c), a method is provided which includes measuring a first test current, a second test current, and a third test current where the first test current occurs before the second test current and the third test current occurs after the second test current. An equation is provided to identify double-dosing events based on two times the absolute value of the second test current minus the absolute value of first test current and minus the absolute value of the third test current. The equation may be in the form of Equation 12 for calculating a summation value Y for determining whether a double-dosing event had occurred.

$$Y=2*abs(i(t))-abs(i(t-x))-abs(i(t+x)) \qquad \text{Eq.12}$$

The terms i(t) is a second test current, i(t−x) is a first test current, i(t+x) is a third test current, t is a time for the second test current, and x is an increment of time in between measurements, and abs represents an absolute function. If the summation value Y is greater than a predetermined threshold, then the test meter may output an error message due to a double-dosing event. The predetermined threshold may be set to a different value for the first time interval $T_1$, the second time interval $T_2$, and the third time interval $T_3$.

In one embodiment, the predetermined threshold may be about 2 microamperes for the first time interval $T_1$, about 2 microamperes for the second time interval $T_2$, and about 3 microamperes for the third time interval $T_3$. The predetermined thresholds may be adjusted as a result of the various factors such as, for example, noise in the test meter, frequency of test current measurements, the area of the electrodes, the distance between the electrodes, the probability of a false positive identification of a double-dosing event, and the probability of a false negative identification of a double-dosing event. The method of identifying the double-dosing event using Equation 12 can be performed for multiple portions of the test current transient. It should be noted that Equation 12 can be more accurate than Equation 11 for identifying double-dosing events because the first test current and third test current provide a baseline correction. When using the test voltage waveform of FIG. 7, the double-dosing check can be performed at a time period just after the beginning of the first, second, and third time intervals because a peak typically occurs at the beginning of the time intervals. For example, the test currents measured at zero seconds to about 0.3 seconds, about 1.05 seconds, and about 4.05 seconds should be excluded from the double-dosing check.

Maximum Current Check

Figure 13:
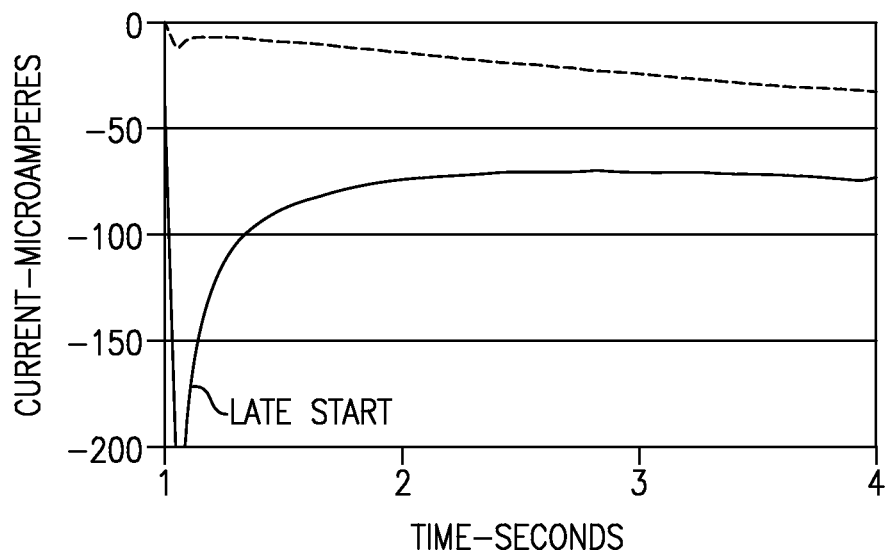
FIG. 13 shows a test current transient of the second test time interval when a late start error occurs (solid line) and does not occur (dotted line) with the test meter.

As referred to in steps 1012a, 1012b, and 1012c of FIG. 11, a maximum current check can be used to identify a test meter error or a test strip defect. An example of a test meter error occurs when the blood is detected late after it is dosed. An example of a defective test strip occurs when the first and second electrodes are shorted together. FIG. 13 shows a test current transient where the test meter did not immediately detect the dosing of blood into the test strip (see solid line). In such a scenario, a late start will generate a significant amount of ferrocyanide before the second test voltage $V_2$ is applied causing a relatively large test current value to be observed. In contrast, when the test meter properly initiates the test voltage waveform once blood is applied, the test current values for the second time interval are much smaller, as illustrated by the dotted line in FIG. 13.

A late start event can cause an inaccurate glucose reading. Thus, it would be desirable to identify a late start event and then have the meter output an error message instead of outputting an inaccurate reading. A late start event causes the measured test current to be larger in magnitude because there is more time for the reagent layer to generate ferrocyanide. Thus, the increased test current values will likely distort the accuracy of the glucose concentration.

In addition to a test meter error, a short between the first and second electrode can cause the test current to increase. The magnitude of this increase depends on the magnitude of the shunting resistance between the first and second electrode. If the shunting resistance is relatively low, a relatively large positive bias will be added to the test current causing a potentially inaccurate glucose response.

Maximum current check (1012a, 1012b, and 1012c) can be performed by comparing the absolute value of all of the measured test current values to a predetermined threshold and outputting an error message if the absolute value of one of the measured test current values is greater than the predetermined threshold. The predetermined threshold can be set to a different value for the first, second, and third test time intervals ($T_1$, $T_2$, and $T_3$). In one embodiment, the predetermined threshold may be about 50 microamperes for the first time interval $T_1$, about 300 microamperes for the second time interval $T_2$, and about 3000 microamperes for the third time interval $T_3$.

Minimum Current Check:

As referred to in steps 1014b and 1014c of FIG. 11, a minimum current check can be used to identify various potential issues, such as, for example, a false start of a glucose test, an improper time shift by a test meter, and a premature test strip removal. A false start can occur when the test meter initiates a glucose test even though no sample has been applied to the test strip. Examples of situations that can cause a test meter to inadvertently initiate a test are an electrostatic discharge event (ESD) or a temporary short between first and second electrodes. Such events can cause a relatively large current to be observed for a least a short moment in time that initiates a test even though no liquid sample has been introduced into the test strip.

An inadvertent initiation of a glucose test can cause a test meter to output a low glucose concentration even though no sample has yet been applied to the test strip. Thus, it would be desirable to identify an inadvertent initiation of a glucose test so that the test meter does not output a falsely low glucose reading. Instead, the test meter should provide an error message that instructs the user to re-insert the same test strip or to insert a new test strip for performing the test again.

A time shifting error by the test meter can occur when the third test voltage $V_3$ is applied early or late. An early application of the third test voltage $V_3$ should cause the test current value at the end of the second time interval $T_2$ to be a relatively large current value with a positive polarity instead of a relatively small current value with a negative polarity. A late application of the third test voltage $V_3$ should cause the test current value at the beginning of the third time interval to be a relatively small current value with a negative polarity instead of a relatively large current value with a positive polarity. For both the early and late application of the third test voltage $V_3$, there is a possibility of causing an inaccurate glucose result. Therefore, it would be desirable to identify a time shifting error by the test meter using the minimum current check so that an inaccurate glucose reading does not occur.

A premature removal of a test strip from the test meter before the end of a glucose test can also cause an inaccurate glucose reading to occur. A test strip removal would cause the test current to change to a value close to zero potentially causing an inaccurate glucose output. Accordingly, it would also be desirable to identify a premature strip removal using a minimum current check so that an error message can be provided instead of displaying an inaccurate glucose reading.

The minimum current check may be performed by comparing the absolute value of all of the measured test current values during the second and third time intervals ($T_2$ and $T_3$) to a predetermined threshold and outputting an error message if the absolute value of one of the measured test current values is less than a predetermined threshold. The predetermined threshold may be set to a different value for the second and third test time intervals. However, in one embodiment, the predetermined threshold may be about 1 microampere for the first time interval $T_1$ and the second time interval $T_2$. Note that the minimum current check was not performed for the first time interval because the test current values are relatively small because the first test voltage is close in magnitude to the redox potential of the mediator.

High Resistance Track:

As referred to in step 1022c of FIG. 11, a high resistance track can be detected on a test strip that can result in an inaccurate glucose reading. A high resistance track can occur on a test strip that has an insulating scratch or a fouled electrode surface. For the situation in which the electrode layers are made from a sputtered gold film or sputtered palladium film, scratches can easily occur during the handling and manufacture of the test strip. For example, a scratch that runs from one lateral edge 56 to another lateral edge 58 on first electrode layer 66 can cause an increased resistance between the first contact pads 67 and the first electrode 166. Sputtered metal films tend to be very thin (e.g., about 10 nm to about 50 nm) making them prone to scratches during the handling and manufacture of the test strip. In addition, sputtered metal films can be fouled by exposure to volatile compounds such as, for example, hydrocarbons. This exposure causes an insulating film to form on the surface of the electrode, which increases the resistance. Another scenario that can cause a high resistance track is when the sputtered metal film is too thin (e.g., less than about 10 nm). Yet another scenario that can cause a high resistance track is when the test meter connectors do not form a sufficiently conductive contact to the test strip contact pads. For example, the presence of dried blood on the test meter connectors can prevent sufficiently conductive contact to the test strip contact pads.

Figure 14:
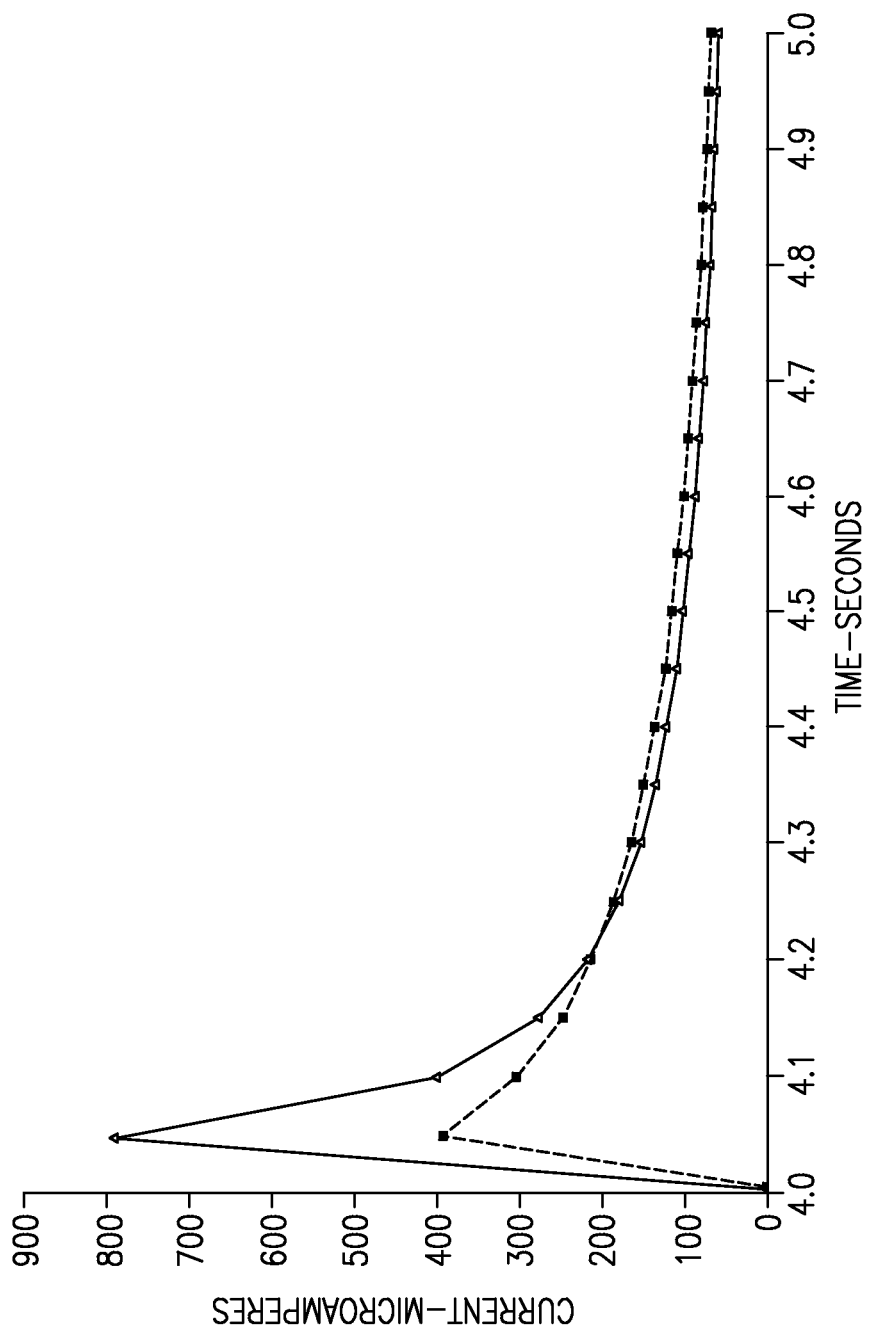
FIG. 14 shows a test current transient of the third test time interval for a test strip having a high resistance track (squares) and a low resistance track (triangles)

FIG. 14 shows two test current transients during a third time interval $T_3$ for a test strip having a high resistance track (squares) and a low resistance track (triangles). A sufficiently high resistance R that is between the electrode and the electrode contact pad can substantially attenuate the magnitude of the effectively applied test voltage $V_{eff}$, which in turn can attenuate the magnitude of the resulting test current. The effective test voltage $V_{eff}$ can be described by Equation 13.

$$V_{eff} = V - i(t)R \qquad \text{Eq.13}$$

$V_{eff}$ will be the most attenuated at the beginning of the third time interval $T_3$ where the test current will generally have the highest magnitude. The combination of a relatively large track resistance R and a relatively large test current at the beginning of the third time interval $T_3$ can cause a significant attenuation in the applied test voltage. In turn, this could cause an attenuation of the resulting test current at the beginning of the third time interval $T_3$, as illustrated in FIG. 14 at t=4.05 seconds. Such attenuation in the peak current immediately at about 4.05 seconds can cause the calculated glucose concentration to be inaccurate. In order to avoid significant attenuation in the applied test voltage, the track resistance R should be a relatively small value (i.e., low track resistance). In one embodiment, a low resistance track may be represented by an electrode layer having a resistivity of less than about 12 ohms per square and a high resistance track may be represented by an electrode layer having a resistivity of greater than about 40 ohms per square.

A determination of whether a test strip has a high track resistance can use an equation based on a first test current $i_1$ and a second test current $i_2$ that both occur during the third time interval $T_3$. The first test current $i_1$ may be measured at about a beginning of the third time interval $T_3$ (e.g., about 4.05 seconds) where the magnitude is at a maximum or close to the maximum. The second test current $i_2$ may be measured at about an end of the third time interval $T_3$ (e.g., about 5 seconds) where the magnitude is at the minimum or close to the minimum.

The equation for identifying a high track resistance may be in the form of Equation 14.

$$R_1 = \frac{i_1}{i_1 - i_2} \qquad \text{Eq. 14}$$

If the first ratio $R_1$ is greater than a predetermined threshold, then the test meter may output an error message due to the test strip having a high resistance track. The predetermined threshold may be about 1.2. It is significant that the first test current $i_1$ is about a maximum current value because it is the most sensitive to resistance variations according to Eq. 13. If a first test current $i_1$ is measured at a time that was closer to the minimum current value, then Equation 14 would be less sensitive for determining whether a high resistance track was present. It is advantageous to have relatively low variation in the first ratio $R_1$ when testing low resistance test strips. The relatively low variation decreases the likelihood of mistakenly identifying a high resistance track test strip. As determined and described herein, the variation of first ratio $R_1$ values for test strips having a low resistance track is about four times lower when a first test current value $i_1$ was defined as a current value immediately after the application of the third test voltage $V_3$, as opposed to being a sum of current values during the third time interval $T_3$. When there is a high variation in first ratio $R_1$ values for low resistance test strips, the probability of mistakenly identifying a high resistance track increases.

Figure 15:
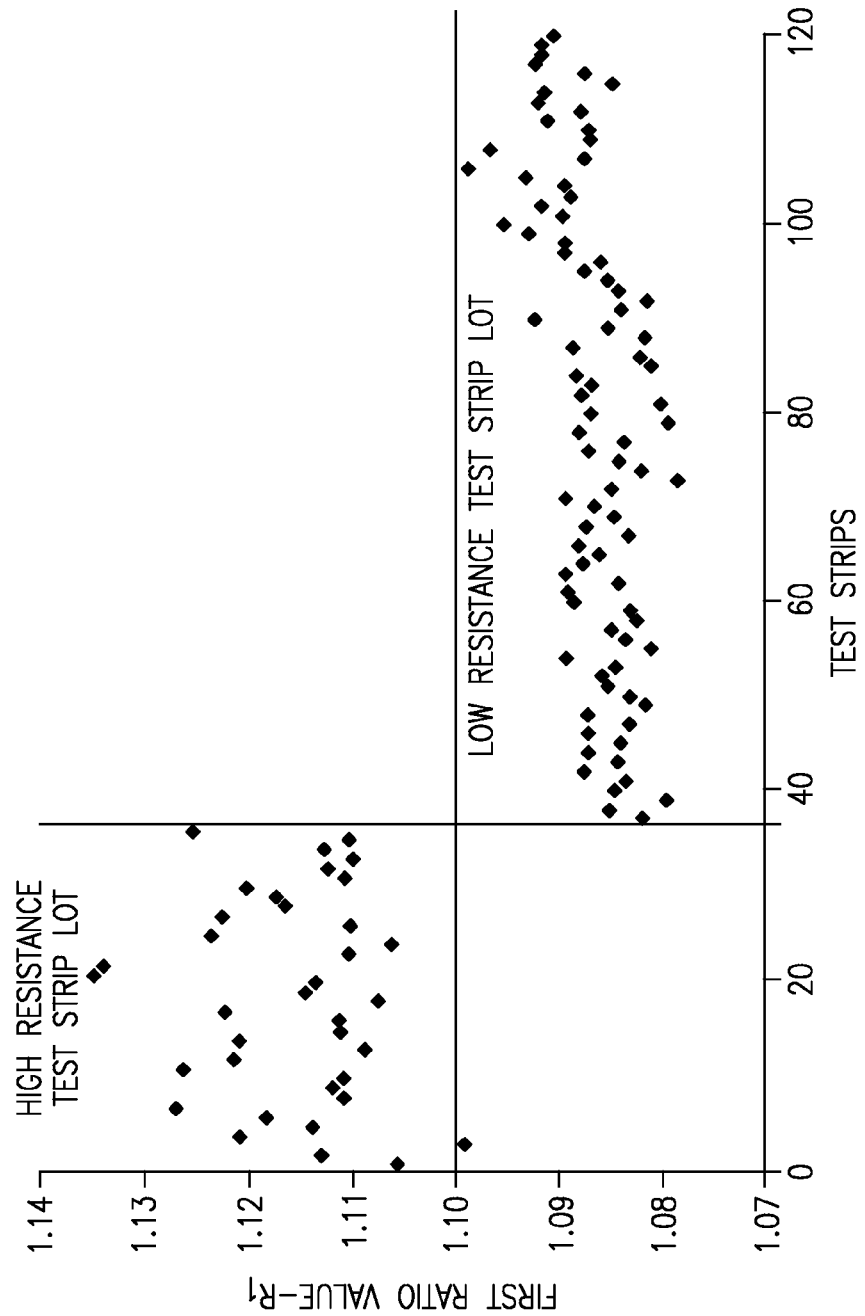
FIG. 15 is a chart showing a plurality of ratio values indicating that a high resistance test strip lot can be distinguished from a low resistance test strip lot.

FIG. 15 is a chart showing a plurality of $R_1$ values calculated with Equation 14 for two test strip lots where one lot has a high resistance track and the other lot has a low resistance track. One lot of test strip was purposely manufactured with a high resistance track by using palladium electrodes that were purposely fouled by an exposure to an atmosphere containing hydrocarbons for several weeks. The second test strip lot was manufactured without purposely fouling the electrode surface. To prevent fouling, a roll of sputtered coated palladium was coated with MESA before coating with the reagent layer. All of the low resistance test strips, which were not fouled, had $R_1$ values of less than about 1.1 indicating that Equation 14 could identify low track resistance test strips. Similarly, essentially all of the high resistance test strips, which were purposely fouled, had $R_1$ values of greater than about 1.1 indicating that Equation 14 could identify high track resistance test strips.

Leakage

As previously referred to in step 1024c in FIG. 11, a leakage can be detected on a test strip when the spacer 60 does not form a sufficiently strong liquid impermeable seal with the first electrode layer 66. A leakage occurs when liquid seeps in between the spacer 60 and the first electrode 166 and/or the second electrode 164. FIG. 4B shows a reagent layer 72 that is immediately adjacent to the walls of the spacer 60. However, in another embodiment (not shown) where leakage is more likely to occur, the reagent layer 72 can have an area larger than the cutout area 68 that causes a portion of the reagent layer 72 to be in between the spacer 60 and the first electrode layer 66. Under certain circumstances, interposing a portion of the reagent layer 72 in between the spacer 60 and the first electrode layer 66 can prevent the formation of a liquid impermeable seal. As a result, a leakage can occur which creates an effectively larger area on either the first electrode 166, which in turn, can cause an inaccurate glucose reading. An asymmetry in the area between the first electrode 166 and the second electrode 164 can distort the test current transient where an extra hump appears during the third time interval $T_3$, as illustrated in FIG. 16.

Figure 16:
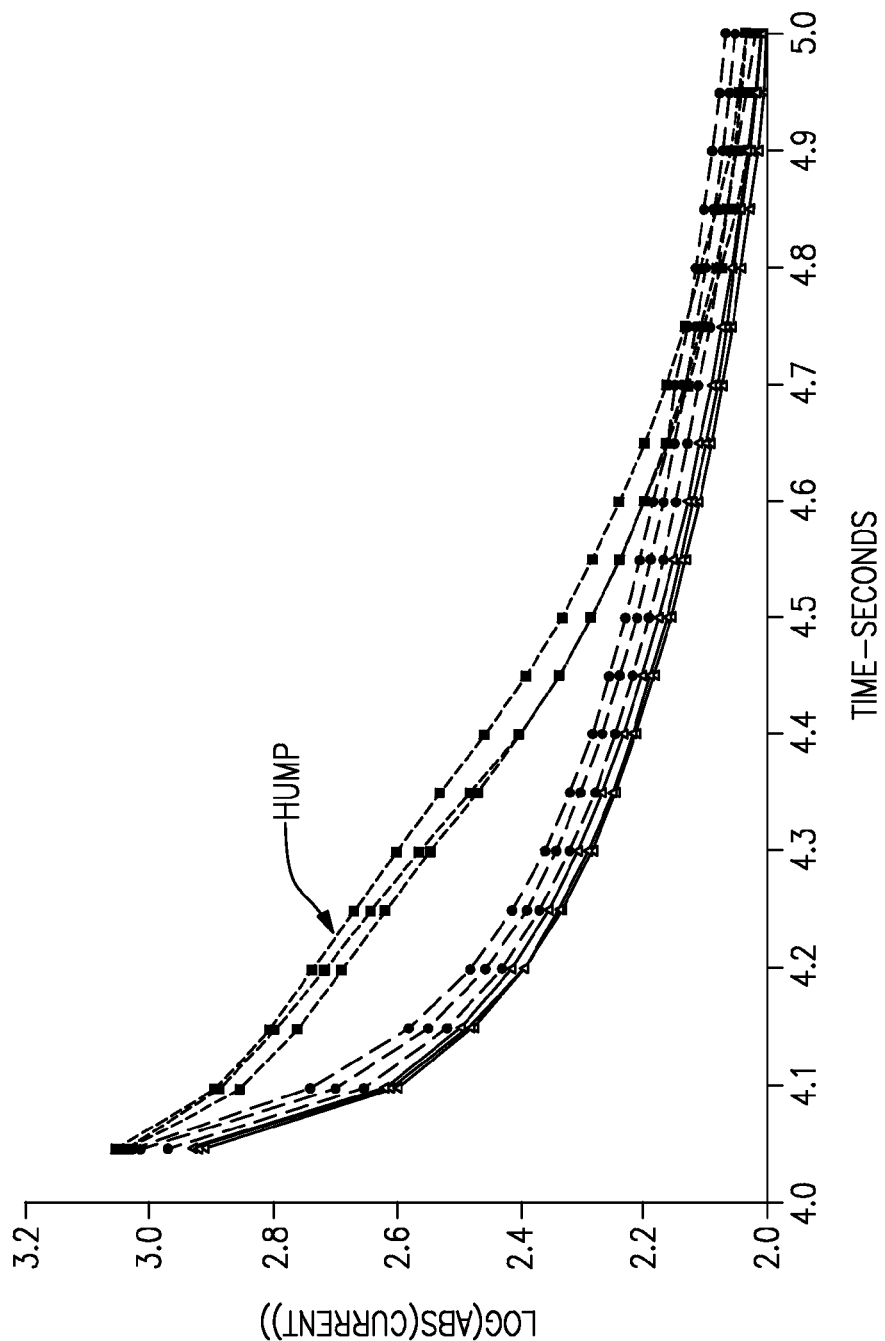
FIG. 16 shows a plurality of test current transients for a test strip lot having leakage between a spacer and the first electrode (squares) and for test strip lots having a sufficiently low amount of leakage (circles and triangles)

FIG. 16 shows test current transients during a third time interval $T_3$ for three different types of test strip lots where test strip lot 1 (squares) has a leakage of liquid between the spacer and the first electrode. Test strip lot 1 was constructed using a dryer setting that did not sufficiently dry the reagent layer and also was laminated with a pressure setting that was not sufficient to form a liquid impermeable seal to the electrodes. Normally, the reagent layer is sufficiently dried so that an adhesive portion of the spacer 60 can intermingle with the reagent layer and still forms a liquid impermeable seal to the first electrode layer 66. In addition, sufficient pressure must be applied so that the adhesive portion of the spacer 60 can form the liquid impermeable seal to the first electrode layer 66. The test strip lot 2 was prepared similarly to test strip lot 1 except that they were stored at about 37° Celsius for about two weeks. The storage of the test strip lot 2 caused the adhesive bond to anneal creating a liquid impermeable seal to the electrodes. Test strip lot 3 was constructed using a dryer setting that was sufficient to dry the reagent layer and also was laminated with a pressure setting sufficient to form a liquid impermeable seal. Both test strip lots 2 and 3 (triangles and circles respectively) show a more rapid decay in the test current magnitude with time compared to test strip 1 (squares), as illustrated in FIG. 16.

A determination of whether a test strip leaks can be performed using an equation based on a first test current, a second test current, a third test current, and a fourth test current that occur during the third test time interval. A first logarithm of a second ratio can be calculated based on a first test current $i_1$ and a second test current $i_2$. A second logarithm of a third ratio can be calculated based on a third test current $i_3$ and a fourth test current $i_4$. An equation may be used to calculate a fourth ratio $R_4$ based on the first logarithm and the second logarithm. If the fourth ratio $R_4$ is less than a predetermined ratio, then the test meter will output an error message due to leakage. The predetermined threshold may range from about 0.95 to about 1. The equation for identifying leakage can be in the form of Equation 15.

$$R_4 = \frac{\log\left(\frac{i_1}{i_2}\right)}{\log\left(\frac{i_3}{i_4}\right)} \quad \text{Eq. 15}$$

In one embodiment, the first test current $i_1$ and the second test $i_2$ current may be about the two largest current values occurring during the third time interval $T_3$. The fourth test current $i_4$ may be a smallest current value occurring during the third time interval $T_3$. The third test current $i_3$ may be selected at a third test time so that a difference between the fourth test time and a third test time is greater than a difference between a second test time and a first test time. In one illustrative embodiment, the first test current, the second test current, the third test current, and the fourth test current may be measured at about 4.1 seconds, about 4.2 seconds, about 4.5 seconds, and about 5 seconds, respectively.

Figure 17:
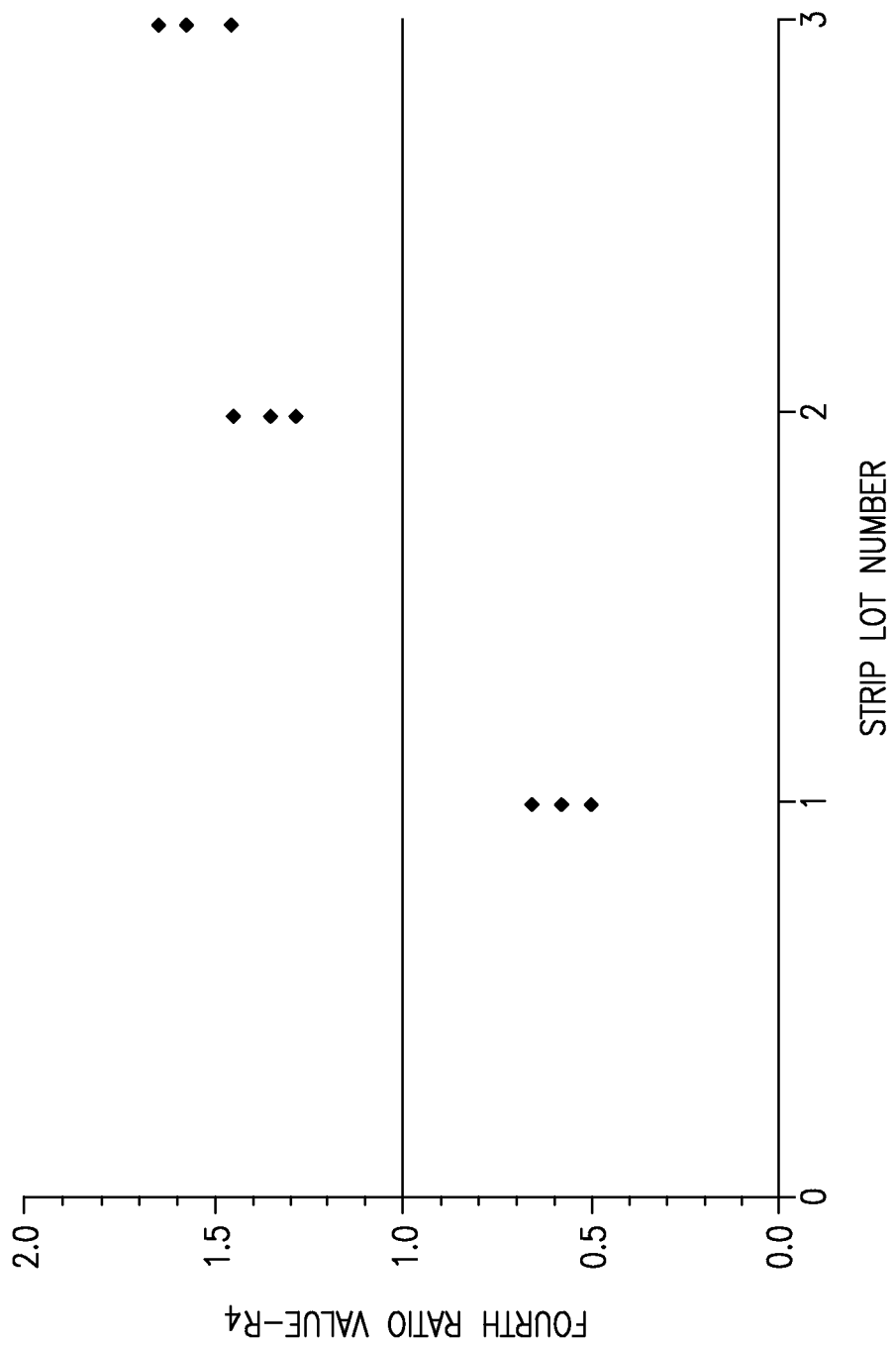
FIG. 17 is a chart showing a plurality of ratio values for identifying leakage of liquid for test strip lots prepared with different manufacturing conditions.

FIG. 17 is a chart showing a plurality of $R_4$ values calculated with Equation 15 for the three test strip lots described for FIG. 16. Accordingly, test strip lot 1 has fourth ratio values less than one and both test strip lots 2 and 3 have fourth ratio $R_4$ values greater than one indicating that Equation 15 can successfully identify strip leakages.

In an alternative embodiment, a determination of whether a test strip has a leakage can be performed using an equation based on three test current values instead of using four test current values as shown in Equation 15. The three test current values may include a first test current $i_1$, a third test current $i_3$, and a fourth test current $i_4$ that all occur during the third test time interval $T_3$. A third logarithm of a fifth ratio may be calculated based on the first test current $i_1$ and the third test current $i_3$. A second logarithm of a third ratio may be calculated based on the third test current $i_3$ and the fourth test current $i_4$. An equation may be used to calculate a sixth ratio $R_6$ based on the third logarithm and the second logarithm. If $R_6$ is less than a predetermined ratio, then the test meter will output an error message due to leakage. The equation for identifying leakage may be in the form of Equation 16.

$$R_5 = \frac{\log\left(\frac{i_1}{i_3}\right)}{\log\left(\frac{i_3}{i_4}\right)} \quad \text{Eq. 16}$$

One skilled in the art will appreciate further features and advantages of the present disclosure based on the above-described embodiments. Accordingly, the present disclosure is not to be limited by what has been particularly shown and described, except as indicated by the appended claims. All publications and references cited herein are expressly incorporated herein by reference in their entirety.

The invention claimed is:

1. A system for determining a processing or system error, the system comprising:
   a test strip having a first electrode and a second electrode defining an electrochemical cell that is sized and configured to receive a sample and further having a reagent layer, including a mediator, disposed on the first electrode, and
   a test meter having a processor programmed with instructions to generate at least one pre-determined voltage between the electrodes for a predetermined amount of time and at least one resulting current of the sample during the pre-determined time, the test meter including a processor for receiving a set of data, the data including at least one applied predetermined voltage and at least one resulting current, wherein the processor is programmed with instructions to utilize the set of data to determine a processing or system error, and in which the processor is programmed with instructions to apply a first test voltage for a first period of time between the first electrode and second electrode sufficient to oxidize a reduced mediator at the second electrode and a second test voltage between the first and second electrode sufficient to oxidize the reduced mediator at the first electrode, the processor being further programmed with instructions to measure a first test current and a second test current occurring during the second test interval wherein the processor is further programmed with instructions to determine whether the test strip has a defect using an equation based on the first test current and second test current.

2. The system according to claim 1, wherein the equation comprises a ratio between the first test current and the second test current.

3. The system according to claim 2, wherein the equation comprises a ratio between the first test current and the difference between the first test current and the second test current.

4. The system according to claim 1, wherein the defect is a high track resistance between a connection point on the test meter and either the first or second electrode of the test strip.

5. The system according to claim 1, wherein the test meter is further configured, using the processor, to measure a first test current, a second test current, a third test current and a fourth test current that occur during the second test interval, wherein the processor is programmed with instructions to calculate a first logarithm of a first ratio based on the first test current and the second test current, a second logarithm of a second ratio based on the third test current and the fourth test current and determining whether the test strip has a defect using an equation based on the first logarithm and the second logarithm.

6. The system according to claim 5, wherein the equation comprises a third ratio based on the first and second ratios.

7. The system according to claim 6, wherein the processor of the test meter is programmed with instructions to generate an error message indicating a defective test strip if the third ratio is less than a predetermined threshold.

8. The system according to claim 5, wherein the defect is a leakage of fluid between a spacer and the first electrode of the test strip.

9. The system according to claim 5, wherein a reagent layer is disposed on the first electrode so that a portion of the reagent layer is between the spacer and the first electrode.

10. The system according to claim 1, wherein the processor of the test meter is further programmed to measure a first test current, a second test current and a third test current, the processor being further programmed to determine whether an error was performed using an equation based on the second test current and a summation of the absolute value of the first test current and the absolute value of the third test current.

11. The system according to claim 1, wherein the system error is indicative of a double dosing event.

12. The system according to claim 1, wherein the system error is indicative of a late start event.

13. The system according to claim 1, wherein the system error is indicative of a false start of a test on the test strip.

14. The system according to claim 1, wherein the analyte is glucose.

* * * * *